United States Patent [19]

Perman et al.

[11] Patent Number: 5,508,060

[45] Date of Patent: *Apr. 16, 1996

[54] METHOD OF POLYMER IMPREGNATION

[75] Inventors: Craig A. Perman, Woodbury; Joanne M. Bartkus; Hye-Ok Choi, both of St. Paul; Manfred E. Riechert, Maplewood; Kelvin J. Witcher, St. Paul; Richard C. Kao, Eden Prairie; James S. Stefely, Woodbury; John E. Gozum, Maplewood, all of Minn.

[73] Assignee: Minnesota Mining and Manufacturing Company, St. Paul, Minn.

[*] Notice: The term of this patent shall not extend beyond the expiration date of Pat. No. 5,340,614.

[21] Appl. No.: 193,170

[22] PCT Filed: Feb. 10, 1994

[86] PCT No.: PCT/US94/01557

§ 371 Date: Sep. 19, 1994

§ 102(e) Date: Sep. 19, 1994

[87] PCT Pub. No.: WO94/18264

PCT Pub. Date: Aug. 18, 1994

Related U.S. Application Data

[63] Continuation-in-part of Ser. No. 16,603, Feb. 11, 1993, Pat. No. 5,340,614.

[51] Int. Cl.$^6$ ............................................. B05D 3/12
[52] U.S. Cl. ...................... 427/2.14; 427/2.24; 427/2.25; 427/2.28; 427/2.3; 427/2.31
[58] Field of Search ............................ 427/430.1, 2.14, 427/2.24, 2.31, 2.3, 2.25, 2.28

[56] References Cited

U.S. PATENT DOCUMENTS 3,773,919  11/1973  Boswell et al. ........................ 424/19
4,147,767  4/1979  Yapel, Jr. ............................... 424/22

(List continued on next page.)

FOREIGN PATENT DOCUMENTS

57091/86  3/1986  Australia ..................... C08J 3/20
2020755  1/1991  Canada .

(List continued on next page.)

OTHER PUBLICATIONS

JAE–JIN Shim et al., J. Phys. Chem. 1991, vol. 95, 353–360.
Alan R. Berens et al., J. Applied Polymer Science, 1992, vol. 46, 231–242.
JAE–SIN Shim et al., AI Ch E Journal 1989, vol. 35(7), 1097–1106.
A. R. Berens et al., Supercritical Fluid Sci. and Tech., ACS Symposium Series, 1989, vol. 406, 207–223.
CRC Handbook of Chemistry & Physics, 67th ed., CRC Press Inc. Boca Raton, Fla., 1987.
Matheson Gas Data Book, 6th ed., Matheson Co., Inc., Lyndhurst, N.J. 1980.
Merck Index, 10th ed., Merck & Co., Rahway, N.J., 1983.
Lange's Handbook of Chemistry, 12th ed., McGraw Hill Book Co., N.Y., N.Y. 1979.
Encyclopedia of Chemical Tech., 3rd Ed., vol. 21, Wiley & Sons, N.Y., N.Y. pp. 377–401, 1984.
Encyclopedia of Chem. Tech. and Encyclopedia of Polymer Science & Engineering, vol. 15, pp. 380–402, 1989.
EPO Journal of Biochemistry, 172:17, 1988 Kawabata, S., et al.

*Primary Examiner*—Shrive Beck
*Assistant Examiner*—Erma Cameron
*Attorney, Agent, or Firm*—Gary L. Griswold; Walter N. Kirn; Carolyn V. Peters

[57] ABSTRACT

Methods of impregnating various polymer substrates with an impregnation additive, by simultaneously contacting the polymer substrate with an impregnation additive, carrier liquid, and supercritical fluid are provided. The impregnation additive is substantially insoluble in the supercritical fluid, and the carrier liquid is preferably substantially insoluble in the supercritical fluid.

2 Claims, 9 Drawing Sheets

U.S. PATENT DOCUMENTS

| | | | |
|---|---|---|---|
| 0200197 | 11/1986 | European Pat. Off. | A61K 7/46 |
| 0222207 | 5/1987 | European Pat. Off. | C08J 3/20 |
| 0401713 | 12/1990 | European Pat. Off. | A61L 15/44 |
| 0405284 | 1/1991 | European Pat. Off. | A61L 29/00 |
| 4,167,589 | 9/1979 | Vitzthum et al. | 426/312 |
| 4,598,006 | 7/1986 | Sand | 424/81 |
| 4,678,684 | 7/1987 | Sand | 427/213.36 |
| 4,820,752 | 4/1989 | Berens et al. | 523/340 |
| 4,992,308 | 2/1991 | Sunol | 427/297 |
| 5,043,280 | 8/1991 | Fischer et al. | 435/235 |
| 5,094,892 | 3/1992 | Kayihan | 407/440 |
| 5,169,687 | 12/1992 | Sunol | 427/297 |
| 5,183,663 | 2/1993 | Greiner | 424/443 |
| 5,340,614 | 8/1994 | Perman et al. | 427/2.24 |

FOREIGN PATENT DOCUMENTS

| | | |
|---|---|---|
| 3906724 | 9/1990 | Germany . |
| 4202320 | 8/1993 | Germany . |
| 9109079 | 6/1991 | WIPO . |
| 9217640 | 10/1992 | WIPO . |

□ BAM (115)
◇ BAM (125)
■ BAM (125)
♦ BAM (135)

□ BAM (120)
♦ BAM (135)
■ BAM (120) + surfactant

METHOD OF POLYMER IMPREGNATION

METHODS OF POLYMER IMPREGNATION

Cross-reference to related application. This is a continuation in part of U.S. Ser. No. 08/016,603, now U.S. Pat. No. 5,340,614 filed Feb. 11, 1993.

FIELD OF THE INVENTION

This invention relates to methods of impregnating polymeric materials with additives utilizing supercritical fluids.

BACKGROUND OF THE INVENTION

A variety of methodologies have been employed in an attempt to impregnate polymers, and in particular thermoplastic polymers, with various impregnation additives. For example, certain polymers can be impregnated with selected additives by immersing the polymers in a solution comprised of the additives for an extended period of time. In addition, it may also be possible to incorporate the additives into polymers during melt processing and/or extrusion. Furthermore, additives may be impregnated into polymers by dissolving the additives into various compounds, such as $CO_2$, $N_2O$, and ethylene, maintained at or near their supercritical temperatures and pressures, and contacting this mixture with the polymer or polymers to be impregnated. Above a defined temperature and pressure, these pressurized compounds form supercritical fluids that serve both as swelling agents for the polymers to be impregnated, and as volatile solvents for additives to be impregnated into the polymers.

Existing methods of impregnating polymers with additives using supercritical fluids are limited by the requirement that the selected additive or additives be soluble in the supercritical fluid, and that the mixture of the additive solubilized in the supercritical fluid be compatible with (i.e. soluble in) the polymer to be impregnated. For example, U.S. Pat. No. 4,598,006 (Sand) discloses a method for impregnating a thermoplastic polymer with an impregnation material (i.e. a fragrance, a pest control agent, or a pharmaceutical composition) by dissolving the impregnation material in a volatile swelling agent (e.g., $CO_2$ maintained at or near supercritical conditions, swelling the thermoplastic polymer by contacting it with the supercritical or nearly supercritical volatile swelling agent containing the impregnation material, and reducing the pressure so the volatile swelling agent diffuses out of the thermoplastic polymer. Among other limitations, Sand teaches that the impregnation material must be soluble in the volatile swelling agent, and that the volatile swelling agent be compatible with (i.e. soluble in) the polymer to be impregnated. Given the lipophilic nature to the volatile swelling agents and polymers disclosed in Sand, the impregnation materials disclosed in Sand are also lipophilic. See also, U.S. Pat. No. 4,678,684; EPO Patent Application Nos. 0 200 197, 0 401 713, 0 405 284; and Australian Patent Application No. 57091/86.

Similarly, U.S. Pat. No. 4,820,752 (Berens et al.) discloses a process for infusing an additive into a polymer by dissolving the additive into a compressed normally gaseous fluid solvent (e.g., $CO_2$) that has a boiling point below room temperature and a density of at least 0.01 g/cc, contacting the solution of the additive and normally gaseous fluid solvent with a polymeric material for a time sufficient to allow at least part of the solution to be absorbed into the polymeric material, and separating the normally gaseous fluid solvent from the polymeric material leaving the additive infused within the polymeric material. Importantly, Berens et al. discloses that the additive must have some degree of solubility in the compressed fluid, and the solution of the compressed fluid and additive must have some degree of solubility in the polymeric material. See also, EPO Patent Application No. 0 222 207.

In addition, supercritical fluids have also been used as a solvent to re-impregnate aromatic components into a tea residue after the caffeine component of the tea had been extracted (U.S. Pat. No. 4,167,589; Vitzthum et al.), as a solvent during the preparation of substance embedded microspheres, by dissolving a substance and polymeric carrier, with or without a liquid medium, into a supercritical gas (U.S. Pat. No. 5,043,280; Fisher et al.), and as a solvent for various monomers or polymers to be impregnated into porous materials, such as wood, to increase the strength and other properties of the porous materials (U.S. Pat. Nos. 4,992,308 and 5,169,687; Sunol).

None of the previously disclosed methods can be used to successfully impregnate additives, and in particular hydrophilic additives, into polymers when the additives are incompatible with (i.e. substantially insoluble in) the supercritical fluid. In fact, to date, no method has been provided for the impregnation of additives into polymers when such additives are substantially insoluble in the supercritical fluid.

SUMMARY OF THE INVENTION

Surprisingly, it has been discovered that impregnation additives that are substantially insoluble in a supercritical fluid can be impregnated into polymer substrates by simultaneously contacting the polymer substrate with the impregnation additive and a carrier liquid, such as water, in the presence of the supercritical fluid. Even more surprisingly, such impregnation can be accomplished using impregnation additives that are incompatible with (i.e. insoluble in) the polymer substrate, and using carrier liquids that are substantially insoluble in the supercritical fluid and/or are incompatible with (i.e. insoluble in) the polymer substrate.

In particular, the present invention provides a method of impregnating a polymeric material with an impregnation additive by simultaneously contacting a polymeric material with a carrier liquid and an impregnation additive, exposing the polymeric material, carrier liquid and impregnation additive to a supercritical fluid in a pressure vessel for sufficient time to swell the polymeric material, such that the carrier liquid and impregnation additive can at least partially penetrate the polymeric material, and releasing the pressure in the pressure vessel so that the carrier liquid diffuses out of the polymeric material, thereby entrapping an amount of the impregnation additive within the polymeric material, wherein the impregnation additive is substantially insoluble in supercritical fluid.

In addition, the present invention also provides a method of impregnating a polymeric material with a hydrophilic impregnation additive by simultaneously contacting a polymeric material with a carrier liquid and a hydrophilic impregnation additive, exposing the polymeric material, carrier liquid and hydrophilic impregnation additive to a lipophilic supercritical fluid in a pressure vessel for sufficient time to swell the polymeric material, such that the carrier liquid and hydrophilic impregnation additive can at least partially penetrate the polymeric material, and releasing the pressure in the pressure vessel so that the carrier liquid diffuses out of the polymeric material, thereby entrapping an amount of the hydrophilic impregnation additive within the polymeric material.

These and various other advantages and features of novelty which characterize the invention are pointed out with particularity in the claims annexed hereto and forming a part hereof. However, for a better understanding of the invention, its advantages, and objects obtained by its use, reference should be had to the accompanying drawings and descriptive matter, in which there is illustrated and described preferred embodiments of the invention.

BRIEF DESCRIPTION OF THE DRAWINGS

The invention may be further illustrated by reference to the accompanying Drawings wherein.

DETAILED DESCRIPTION OF EMBODIMENTS OF THE INVENTION

General Method

Figure 1:
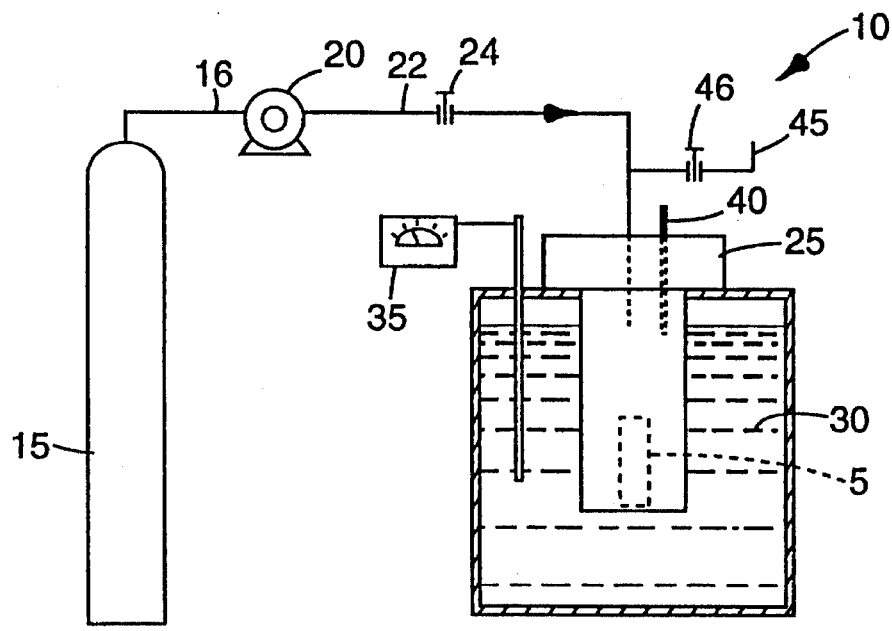
FIG. 1 is a schematic illustration (not to scale) of an impregnation apparatus for impregnating polymers with selective impregnation additives according to the methods of the present invention.

FIG. 1 schematically illustrates an impregnation apparatus 10 for the impregnation of polymers with selected impregnation additives according to the methods of the present invention. The major components of the impregnation apparatus 10, include a tank 15 that holds the material to be used as a supercritical fluid, a compressor 20 to pressurize and transfer the supercritical fluid from the tank 15 to a pressure vessel 25, a water or oil bath 30 in which the pressure vessel 25 is suspended, a temperature regulator 35 to maintain the water/oil bath 30 at a predetermined temperature, a pressure transducer 40 to monitor and maintain the pressure within the pressure vessel 25 at a predetermined level, and a vent line 45, to be used to vent the supercritical fluid from the pressure vessel 25 after impregnation of a polymer has been accomplished.

In use, a polymer sample to be impregnated (not shown) is placed in a container 5, such as a beaker or test tube, within the pressure vessel 25. The polymer sample is covered with a solution of a carrier liquid and one or more impregnation additives (not shown), and maintained completely submerged in this solution via a glass wool plug or other inert material placed in the top of the container 5. The pressure vessel 25 is then sealed, and placed or maintained in water/oil bath 30.

To start the impregnation process, a selected material, such as carbon dioxide, is transferred from tank 15 via line 16 to compressor 20, where it is pressurized to the critical pressure (Pc) of the material, or greater. The compressed material leaves compressor 20 via line 22 and valve 24, and is transferred into the pressure vessel 25 containing the polymer sample to be impregnated, after which valve 24 is closed.

When the pressurized material enters pressure vessel 25, it may already comprise a supercritical fluid, so long as the temperature of the pressurized material exceeds the critical temperature ($T_c$) of the material. However, if the pressurized material has not yet reached or exceeded $T_c$, then water/oil bath 30 can be heated using temperature regulator 35 to rapidly convert the pressurized material into a supercritical fluid capable of swelling the polymer sample according to the methods of the present invention. In this regard, it will be appreciated that both temperature regulator 35 and pressure transducer 40 can be used to maintain pressure vessel 25, including the supercritical fluid, polymer sample, impregnation additive, and carrier liquid contained therein, at a preselected temperature and pressure above the $T_c$ and $P_c$ of the supercritical fluid.

After sufficient time has passed to complete impregnation of an impregnation additive into the polymer sample in container 5, the supercritical fluid contained in pressure vessel 25 is vented from the pressure vessel 25 via vent line 45 by keeping valve 24 closed, and opening valve 46. In this regard, pressure vessel 25 should be vented in a controlled manner (e.g., at a slow regular rate) to prevent damage (e.g., fracturing and/or foaming) to the polymer samples.

It will be appreciated that vent line 45 may be vented directly to the atmosphere, or may be vented into a holding container (not shown), re-circulated to tank 15, as need be. After the supercritical fluid has been vented, pressure vessel 25 can be opened, and the impregnated polymer sample recovered from container 5.

While the impregnation of a polymer sample with one or more impregnation additives according to the methods of the present invention has been illustrated with respect to FIG. 1, it will be appreciated that any apparatus capable of containing a supercritical fluid, polymer sample, carrier liquid, and impregnation additive(s), such that the polymer sample is impregnated with the impregnation additive(s), is considered to fall within the scope of the present invention. In this regard, those skilled in the art will be readily capable of adapting the apparatus illustrated in FIG. 1, such as through the incorporation of a thermocouple into pressure vessel 25, thereby eliminating the need for water/oil bath 30, or in any other manner consistent with the practice of the methods of the present invention.

Supercritical Fluid

As used herein, a supercritical fluid refers to a material maintained at or above its critical temperature ($T_c$) and critical pressure ($P_c$) (i.e. above its critical point ($C_p$)), so as to place the material in a supercritical fluid state. Typically, supercritical fluids are gases at ambient temperature (approximately 22° C.) and pressure (approximately 1.01 mega Pascals (MPa)). However, when maintained at or above $C_p$, the supercritical fluid displays properties of both a gas and a liquid. In particular, such a supercritical fluid has the solvent characteristics of a liquid, but the low surface tension of a gas. Accordingly, as with a gas, the supercritical fluid can more readily diffuse into a selected solute material, such as a polymer.

Figure 2:
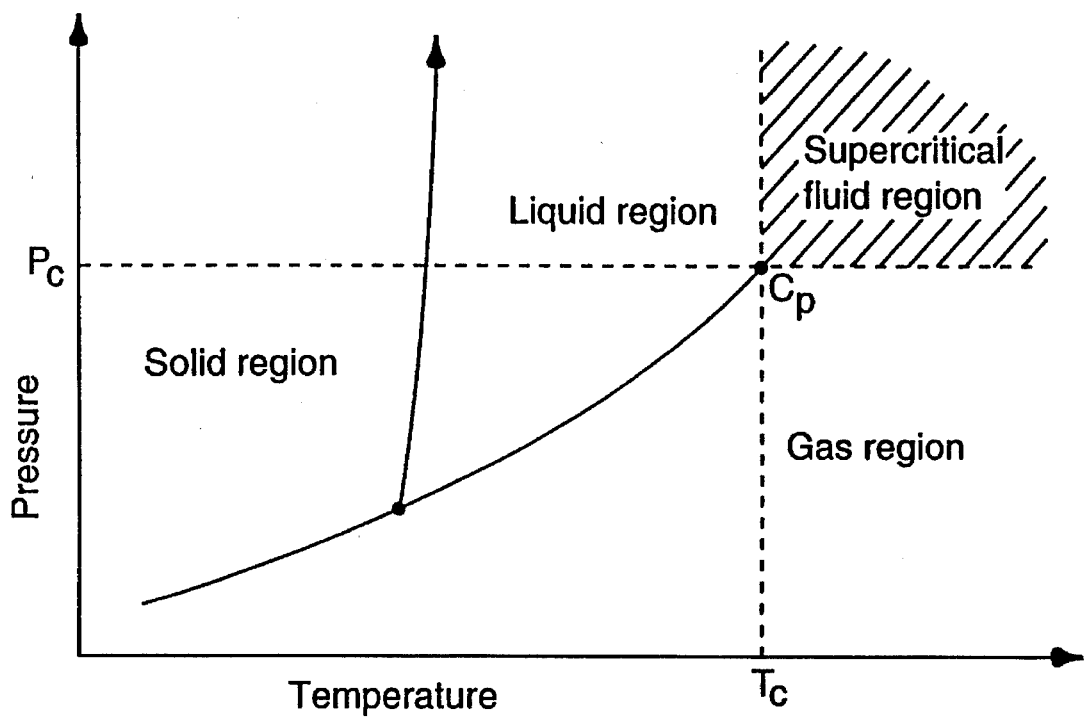
FIG. 2 is a diagram illustrating the various states of matter of a material capable of forming a supercritical fluid useful in the method of the present invention.

FIG. 2 diagrammatically illustrates the various states of matter of a typical material capable of forming a supercritical fluid. At appropriate temperatures and pressures the selected material may take the form of a solid, a liquid, or a gas. However, above a defined $T_c$ and $P_c$, the material takes the form of a supercritical fluid displaying the properties noted above. Thus, the supercritical fluid region for such a material is defined by the shaded region of FIG. 2, encompassing all temperatures and pressures beyond the $C_p$ of the material.

Table 1 lists several nonlimiting examples or supercritical fluids, including their critical temperatures and pressures, that are useful in the methods of the present invention.

TABLE 1

Critical temperatures ($T_c$) and critical pressures ($P_c$) of selected supercritical fluids.

| Supercritical Fluid | $T_c$ in °C. | $P_c$ in MPa |
| --- | --- | --- |
| carbon dioxide | 31.1 | 7.38 |
| nitrous oxide | 36.5 | 7.26 |
| ethylene | 9.3 | 5.03 |
| ethane | 32.3 | 4.88 |
| chlorotrifluoromethane | 29.9 | 3.92 |

In addition to the supercritical fluids listed in Table 1, a large number of other materials are also useful in the methods of the present invention, including without limitation, nitrogen, propane, propylene, cyclohexane, isopropanol, benzene, toluene, p-xylene, ammonia, water, methane, trichlorofluoromethane, tetrafluoroethylene, perfluoroethane, tetrafluoromethane, trifluoromethane, and 1,1 difluoroethylene. The specific $T_c$ and $P_c$ for each of these materials, and for any other supercritical fluid useful in the methods of the present invention, are readily obtainable in a number of standard references, including the CRC Handbook of Chemistry and Physics, 67th ed., CRC Press Inc., Boca Raton, Fla., 1987, Matheson Gas Data Book, 6th ed., Matheson Co., Inc., Lyndhurst, N.J., 1980, Merck Index, 10th ed., Merck and Co., Rahway, N.J., 1983, and Lange's Handbook of Chemistry, 12th ed., McGraw Hill Book Co., New York, N.Y., 1979, the disclosures of which are herein incorporated by reference. Furthermore, it is also contemplated that mixtures of two or more supercritical fluids could also be used in the methods of the present invention.

While any of a variety of supercritical fluids are useful in the methods of the present invention, it is preferred that the supercritical fluid be substantially nonreactive and nontoxic (i.e. inert) with respect to the impregnation additives, carrier liquids, and polymers used in the methods of the present invention. In fact, the relative inertness of the supercritical fluid used in the methods of the present invention is particularly important with many of the biologically active additives impregnated into polymers according to the methods of the present invention. For example, when impregnating an active polypeptide (e.g. insulin) into a polymer substrate, a reactive supercritical fluid could inhibit or completely destroy the desired biological activity of such a polypeptide. Likewise, a toxic supercritical fluid may remain as a residual additive within the polymer substrate along with the impregnated polypeptide. Under either or both scenarios, the usefulness of impregnating such a polypeptide additive into a polymer substrate would be compromised or lost.

Other factors that can influence the selection of a supercritical fluid for use in the methods of the present invention include cost of the supercritical material, solubility of the supercritical material in the polymer to be impregnated and the carrier liquid, as well as the practical working limits of the $T_c$ and $P_c$ of the supercritical fluid. In this regard, it is preferred that the $T_c$ of the supercritical fluid be as close as possible to ambient conditions (e.g. approximately 22° C.), such that the supercritical fluid can be maintained at a temperature of from about 0° C. to about 100° C., preferably from about 20° C. to about 90° C., and most preferably from about 30° C. to about 80° C. These preferred temperature limits will prove particularly important with respect to biologically active additives, such as the active polypeptides noted above, which can be particularly susceptible to thermal degradation at temperatures in excess of about 40° C.

The preferred limits on the $P_c$ and the operating pressures of the supercritical fluid used in the methods of the present invention are practical in nature. For example, the upper limits of the operating pressures will be dictated, among other things, by the cost and availability of equipment capable of containing pressures in excess of 138 MPa (20,000 psi), as well as the susceptibility of the impregnation additive and/or polymer to degradation at higher pressures. In this regard, it is preferred that the supercritical fluid be maintained at pressures from about 4 MPa to about 138 MPa, preferably from about 5 MPa to about 45 MPa, and most preferably from about 7 MPa to about 30 MPa. As with the preferred temperature limitations noted above, biologically active additives will preferably be subjected to the minimum critical pressures necessary to ensure impregnation according to the methods of the present invention.

With respect to the solubility of the supercritical fluid in the polymer or polymers to be impregnated by the methods of the present invention, it is preferred that the selected supercritical fluid show minimal solubility in the polymer to be impregnated. Thus, the supercritical fluid should have sufficient solubility to swell the polymer matrix, and thereby allow for the penetration of the carrier liquid and impregnation additive therein, but not provide such a degree of solubility that the polymer matrix loses its form and/or dissolves substantially into the supercritical fluid.

Given the requirements outlined above, supercritical carbon dioxide provides a particularly preferred supercritical fluid for use in the methods of the present invention. Supercritical carbon dioxide is a low cost, inert, material displaying a $T_c$ of 31.1° C. and a $P_c$ of 7.38 MPa. Furthermore, supercritical carbon dioxide displays sufficient solubility to swell a wide variety of polymeric materials, including both homopolymers and copolymers, such as polyethylene, polypropylene, polyamide, polyurethane, silicone, albumin, lactic acid polymers, and glycolic acid polymers, without dissolving or otherwise dissociating the polymer matrix.

Impregnation additives

The impregnation additive can comprise any element, compound or composition capable of being impregnated into a polymer using a supercritical fluid and a carrier liquid according to the present invention, so long as the impregnation additive is substantially insoluble in the supercritical fluid. As used herein, an impregnation additive is substantially insoluble in a supercritical fluid when none or virtually none of the impregnation additive will dissolve into the supercritical fluid at a predetermined temperature and pressure above the $C_p$ of the supercritical fluid. In this regard, an impregnation additive will be considered to be substantially insoluble in a supercritical fluid, so long as no more than an insignificant quantity, not readily detected by conventional means, dissolves into the supercritical fluid.

Nonlimiting classes of impregnation additives useful in the methods of the present invention include dyes, monomers, drugs, proteins, polypeptides, nucleotides, and combinations thereof. Preferably, the impregnation additive will comprise a biologically active drug, polypeptide, or protein, including enzymes, hormones, antibiotics, anti-inflammatory agents, analgesics, calcium channel blockers, beta-blockers, antidepressants, antacids, antidiabetics, cerebral stimulants, sedatives, anti-parasitics, decongestants, muscle relaxants, anti-Parkinsonism agents, antiviral agents, bronchodilators, vitamins and dietary supplements and the like. Nonlimiting examples of suitable polypeptides and proteins useful as impregnation additives in the methods of the present invention include immunomodulators such as Thymic Humoral Factor, growth Factors such as Human Growth Factor and Fibroblast Growth Factor, antitumorals such as BCNU and epirubian, hormones such as LHRH, and steroidals such as medroxyprogesterone acetate and magestrol acetate.

In an alternative embodiment of the present invention, the impregnation additive comprises one or more monomers, such as acrylic acid, ethylene, or propylene. In this embodiment, a polymer substrate undergoes a series of impregnations with one or more monomers followed by a polymerization of such monomers in situ to increase the strength, modulus, or other properties of the polymer substrate.

Preferably, the impregnation additive according to the present invention is substantially insoluble over the entire critical temperature and pressure ranges of the supercritical fluid used in the methods of the present invention. However, it is to be understood that the impregnation additive need only be substantially insoluble in a supercritical fluid maintained at a set temperature and pressure to be considered within the scope of the present invention.

One method of determining the insolubility of an impregnation additive in a supercritical fluid is to compare the solubility parameter of the impregnation additive with that of the supercritical fluid at a set temperature and pressure, or over a temperature and pressure range. When the solubility parameter for a solvent and a solute are within about 1 $(cal/cc)^{1/2}$, then complete miscibility between the solvent and solute will generally occur. As the difference between the solubility parameters of the solvent and solute increase, the solute will becoming increasingly less soluble in the solvent, until a point is reached where the solute is substantially insoluble in the selected solvent.

The solubility parameters of most materials are readily available and/or determinable by those skilled in the art. In this regard, such parameters can typically be found in a number of standard references, including Volume 21 of the *Encyc. of Chemical Technology*, 3rd ed., Wiley & Sons, New York, N.Y., pp. 377–401, 1984, the disclosures of which are herein incorporated by reference. Even when such parameters are not available in a standard reference, they can be estimated using standard equations for solubility parameters, such as Giddings equations. For a more through discussion of solution chemistry and estimation of solubility parameters, reference should be had to Volume 21 of the *Encyc. of Chem. Tech.* and the *Encyc. of Polymer Science and Engineering*, Vol. 15, pp 380–402, 1989, the disclosures of which are herein incorporated by reference.

Even when the solubility parameters of an impregnation additive and/or supercritical fluid cannot be readily obtained, the solubility, or lack thereof, of the impregnation additive in the supercritical fluid can be determined by a simple series of tests utilizing an apparatus, such as the impregnation apparatus illustrated in FIG. 1 herein. Specifically, in a first test, the impregnation additive and polymer to be impregnated can be placed in separate open containers 5 and 5' (not shown) inside of pressure vessel 25, which is then charged with the selected supercritical fluid at a predetermined temperature and pressure. After a predetermined period of time, typically an hour or more, the pressure vessel 25 is vented via vent line 45, and the polymer and impregnation additive removed.

At the same or different time, in a second test, the impregnation additive and polymer should be simultaneously contacted with a carrier liquid in pressure vessel 25 using the same supercritical fluid and conditions according to the method of the present invention. Thereafter, the pressure vessel 25 is vented via vent line 45, and the polymer removed.

Both polymer samples can then be visualized or otherwise assayed by means well known to those skilled in the art to determine whether or not the impregnation additive impregnated the polymer sample. If the polymer sample subjected to the method of the present invention shows impregnation, but the polymer sample maintained in separate containers does not, then it can be concluded that the impregnation additive was insoluble in the supercritical fluid at the selected conditions, and accordingly, that only the method of the present invention can provide for the impregnation of the polymer with the impregnation additive at the given temperature and pressure conditions.

Carrier liquids

The carrier liquid used in the method of the present invention is normally a liquid at atmospheric pressures and room temperature, and will typically remain a liquid during contact with the supercritical fluid. Preferably, the carrier liquid should be capable of partially or completely dissolving (i.e., forming a solution with) the impregnation additive to be impregnated into a polymer substrate according to the methods of the present invention. However, solubility of the impregnation additive into the carrier liquid is not required to practice the method of the present invention. Thus, in addition to true ionic or molecular solutions of the carrier liquid and impregnation additive, colloidal suspensions and two-phase dispersions of the impregnation additive and carrier liquid are also considered to fall within the scope of the methods of the present invention.

As with the selected supercritical fluid, the carrier liquid will preferably be low cost, and inert (i.e. nonreactive and nontoxic) with respect to the impregnation additive, polymer substrate, and supercritical fluid. In addition, the carrier liquid will preferably be substantially insoluble in the polymer to be impregnated, but at the very least, the carrier liquid must not dissolve or otherwise dissociate the polymer substrate to be impregnated. Furthermore, it is also preferable that the carrier liquid does not have a high degree of solubility in the supercritical fluid under the process conditions, as the carrier liquid would then evaporate from the impregnation additive/carrier liquid solution, leaving a dry or nearly dry impregnation additive incapable of forming a solution with the supercritical fluid, and therefor incapable of impregnating the chosen polymer.

Given the above requirements, water is the preferred carrier liquid for use in the methods of the present invention. Water is a low cost, inert liquid, that is poorly soluble or insoluble in most supercritical fluids and polymers to be impregnated. In addition, water is an excellent solvent for a wide variety of ionic compounds, and is readily capable of forming molecular solutions, colloidal suspensions, and various two phase dispersions.

A variety of other carrier liquids may also be used in the methods of the present invention, including, without limitation, methanol, ethanol (ETOH), hexane, and combinations thereof. All of these carrier liquids typically suffer from one or more disadvantages (e.g. toxicity, reactivity, cost, solubility in the polymer substrate, and/or solubility in the supercritical fluid) with respect to water, that make them less preferred in the methods of the present invention. However, some of these shortcomings may be overcome or diminished by using various mixtures of carrier liquids (e.g a mixture of water and ETOH) as the carrier liquid component in the methods of the present invention.

For example, ETOH can serve as a useful carrier liquid in the methods of the present invention, particularly when the impregnated polymer is being employed in a nonbiological system. In addition to potential toxicity problems, ETOH is also somewhat soluble in typical supercritical fluids, such as supercritical carbon dioxide. Thus, when ETOH is employed as a carrier liquid, excess ETOH should be placed in the pressure vessel, such that a saturated solution of ETOH in the supercritical fluid is formed during processing. By maintaining a saturated environment within the pressure vessel, the polymer to be impregnated will remain immersed in the ETOH/impregnation additive solution throughout processing, thereby ensuring impregnation of the impregnation additive into the polymer substrate.

Polymers

Virtually any swellable polymeric material, including both homopolymers and copolymers, is useable in the methods of the present invention. Nonlimiting examples of polymeric materials useful in the method of the present invention include polyolefins, polyamides, polyimides, polyesters, polyurethanes, polyacrylates, polycarbonates, polyacetylenes, polyisoprene polymers, polystyrenes, styrenebutadiene polymers, chloroprene polymers, polyetheramides, vinyl chloride polymers, vinylidene chloride polymers, natural rubbers, butyl rubbers, nitrile rubbers, silicone, polyvinyl alcohol polymers, cellulose derivative polymers, protein derivative polymers (e.g., albumin), lactic acid polymers, glycolic acid polymers, and combinations thereof. Preferred polymers include, without limitation, low density polyethylene, linear low density polyethylene, polypropylene, polyamide, polymers, albumin (e.g., BSA), and polymers prepared from lactic acid alone, glycolic acid alone, or lactic acid and glycolic acid copolymers.

Advantageously, the polymeric substrates can be impregnated without altering or compromising the pre-impregnate shape and dimensions of the polymeric substrate. For example, polymeric sutures, films, beads and the like can be formed and then impregnated. This is particularly advantageous when impregnating materials that are susceptible to degradation at temperatures typically associated with formation extrusion, coating, molding and the like of the polymeric substrate.

Process parameters and Advantages

While not being held to a theory of operation, it is believed that the method of the present invention functions to impregnate polymer substrates with an impregnation additive in a significantly different manner than that of the prior art. In the prior art methods, the supercritical fluid serves both as a solvent for the additive and as a swelling agent for the polymer to be impregnated. In contrast, in the methods of the present invention, the impregnation additive is substantially insoluble in the supercritical fluid. Therefore, the supercritical fluid acts only to swell the polymer, after which the impregnation additive solubilized in the carrier liquid impregnates or otherwise diffuses into the polymer substrate. Thus, it is believed that only the intimate simultaneous contact of an impregnation additive solubilized in the carrier liquid with the swollen polymer substrate will allow for the impregnation of the impregnation additive into the polymer substrate.

After the impregnation additive and carrier liquid impregnate the swollen polymer substrate, the pressure in the pressure vessel containing the polymer and supercritical fluid is slowly reduced. It is believed that the gradual release of the pressure decreases the swelling of the polymer, thereby entrapping an amount of the impregnation additive within the polymer substrate. For example, when an ionic or molecular solution of a carrier liquid and impregnation additive (the CL/IA solution), impregnate a swollen polymer, the gradual shrinking of the swollen polymer by releasing the pressure in the pressure vessel, resulting in the precipitation or other deposition of the impregnation material from the CL/IA solution, eventually entrapping the impregnation additive within the polymer matrix, without gross deformation or degradation of the polymer matrix.

Since the carrier liquid acts to transport the impregnation additive within the polymer matrix, the methods of the present invention should function whether the impregnation additive forms an ionic or molecular solution, a colloidal suspension, or a two phase dispersion with the carrier liquid. With a colloidal suspension or two-phase dispersion, the mixture of the impregnation additive and carrier liquid may require pulsating or continuous agitation during impregnation to ensure that the additive remains essentially evenly dispersed or suspended in the carrier liquid. Absent such agitation, it is believed that an ionic or molecular solution of the impregnation additive in the carrier liquid will be a preferred manner of practicing the method of the present invention.

A number of parameters and characteristics of the selected supercritical fluid, impregnation additive, carrier liquid, and polymer substrate influence the degree to which the impregnation additive impregnates the polymer substrate. For example, three important variables, temperature, pressure, and time, come into play during the impregnation of a polymer substrate by an impregnation additive.

In general, the higher the temperature employed during impregnation, the greater the swelling of the polymer substrate. This in turn has the capacity to increase the amount of impregnation additive entering the polymer substrate. However, as noted above, the ability to use higher impregnation temperatures is tempered, among other things, by the susceptibility to the impregnation additive to thermal degradation. Thus, many biologically active materials, and in particular biologically active polypeptides, are readily subject to thermal degradation. Furthermore, the susceptibility of the polymer substrate to thermal degradation and/or melting will also place a practical limit on the temperatures employed in polymer impregnation.

In a similar fashion, the pressures employed during polymer impregnation are also limited by practical considerations. While increased pressures generally lead to increased swelling of the polymer substrate, a point is reached where the surface pressure exerted by the supercritical fluid at very high pressures may counteract the increased swelling of the polymer substrate, thereby placing a practical cap on the pressures that can or should be employed in such a method. In addition, it is known that many biologically active materials, such as polypeptides, degrade or otherwise lose their activity when exposed to high pressure conditions, particularly over an extended period of time. Accordingly, such materials should be impregnated at as low a pressure as possible, while still staying at or above the $P_c$ of the supercritical fluid being used in the methods of the present invention.

In general, longer periods of exposure to a supercritical fluid at supercritical conditions will favor deeper penetration of an impregnation additive into a polymer substrate. In this regard, the need to utilize relatively long periods of exposure will prove particularly necessary the larger and thicker the polymer substrate to be impregnated. For example, a 3 mm in diameter polyethylene bead, having a relatively large surface area, may require approximately two hours in which to impregnate an aqueous dye solution (e.g. rose bengal dye) to its core, while a 2.5 cm×2.5 cm×0.5 cm thick polyethylene film may require in excess of 6 hours of exposure to the impregnation conditions to achieve the same degree of penetration as the polyethylene bead. However, the total period of exposure to impregnation conditions will always have to be balanced against the degree of degradation of the impregnation additive and/or polymer substrate resulting from prolonged exposure at the chosen temperature and pressure conditions employed.

Several characteristics or properties of the polymer, such as the crystallinity, density, orientation, and amount of crosslinking appear to influence the degree to which any given polymer can be impregnated with an impregnation additive. In general, the higher the density, crystallinity, orientation and crosslinking of the polymer substrate, the more rigorous the conditions needed to successfully impregnate an impregnation additive into a polymer substrate. Thus, a low density, nonoriented polymer that is highly amorphous and non-crosslinked in structure should be relatively easier to impregnate with a given additive than a similar high density, oriented, crystalline polymer with a relatively high degree of crosslinking.

The methods of polymer impregnation of the present invention provide a number of advantages over presently available methods. Principal among these is the ability to impregnate additives which are substantially insoluble in the supercritical fluid swelling agent. To date, existing methods have required the impregnation material to be capable of forming a solution with the supercritical fluid in order to impregnate the impregnation material into a polymer substrate. Thus, only the methods of the present invention can provide for the impregnation of this class of materials into polymer substrates.

The ability of a carrier liquid to transport an impregnation additive into a polymer matrix swollen by exposure to a supercritical fluid provides for the incorporation of incompatible additives and polymer substrates. Thus, hydrophilic impregnation additives, such as rose bengal dye, can be impregnated into hydrophobic polymers such as polyethylene, polypropylene, and polyurethane via the methods of the present invention. In this regard, such hydrophilic impregnation additives could not be impregnated using existing supercritical methods, since these additives are incompatible (i.e., insoluble) with both the lipophilic supercritical fluid (e.g., supercritical $CO_2$) and the hydrophobic polymer substrates. Furthermore, it will also be appreciated that the preferred carrier liquid of the present method is water, which is likewise incompatible with preferred supercritical fluids and hydrophobic polymer substrates.

Though the method of the present invention utilizes impregnation additives that are substantially insoluble in the supercritical fluid, it will be appreciated that the use of carrier liquids according to the present invention could enhance the impregnation of additives with a low degree of solubility in the supercritical fluid. In addition, the method of the present invention may also prove useful to impregnate additives with gaseous mediums, such as $CO_2$, maintained below their $C_p$ (i.e., subcritical). In this regard, as long as the pressurized gaseous medium is capable of swelling the polymer substrate, the intimate simultaneous contact of the impregnation additive, carrier liquid, and swollen polymer substrate should allow the carrier liquid to transport the additive into the polymer matrix, albeit at a somewhat reduced level than would be accomplished using a supercritical fluid.

Use of supercritical $CO_2$ as the preferred supercritical fluid, and water as the preferred carrier liquid will also result in a number of advantages. Both $CO_2$ and water are low cost, inert (e.g., nonreactive and nontoxic) materials, that are easy and safe to work with, and in most instances will have no deleterious effects on either the polymer substrate or impregnation additive.

In addition, water is an excellent solvent or dispersing medium for many impregnation additives, but is substantially insoluble in supercritical $CO_2$ over a wide range of temperature and pressure conditions. Furthermore, the $T_c$ of $CO_2$ is relatively close to ambient conditions, such that a wide variety of biologically active additives can be impregnated into polymer substrates without significantly altering their desired biological activity.

The fact that the impregnation additives of the present invention are substantially insoluble in the supercritical fluids allows for the impregnation of several different additives into polymer substrates at the same time, without unwanted cross-contamination between the various samples. In addition, this same property, in combination with an inert carrier liquid such as water, will allow for complete recovery of often costly unimpregnated additives after the impregnation process is complete. Further, the use of a carrier liquid will, in many cases, prevent the unwanted extraction of various components, such as plasticizers and tackifiers, from the polymer substrates during the impregnation process.

The invention will be further illustrated by reference to the following non-limiting Examples. All parts and percentages are expressed as parts by weight unless otherwise indicated.

EXAMPLES 1, and 5–10, and

Comparative Examples 2–4, and 11–13

Five gram samples of various polymeric materials were placed in an open glass vial in a 300 cubic centimeter MICRO SERIES™ pressure vessel (2%16 inch outside diameter, 11¾ inch overall length; Newport Scientific, Inc., Jessup, Md.). The specific polymeric materials utilized included, ASPEN™ 6806 polyethylene (PE) beads (3 mm diameter; melt index=105° C., linear low density polyethylene; Dow Chemical Co., Midland, Mich.), No. 3145 polypropylene (PP) beads (3 mm diameter; melt index=300°

C.; Exxon Chemical Co., Darien, Conn.), and No. 19, 105-1 polyamide pellets (PA) (3 mm diameter; melt index=95° C.; Aldrich Chemical Co., Milwaukee, Wis.). The polymeric materials were contacted with, or remained separate from, an impregnation additive consisting of 0.25 g of rose bengal dye (Aldrich Chemical Co.) in either a dry, powdered form, or in a solution or dispersion of 0.25 g of rose bengal dye in 15 ml of various carrier liquids, including deionized water, hexane, or ethyl alcohol (ETOH). A glass wool plug was used to keep the beads and pellets submerged in the dye/carrier liquid solutions.

After placement of the polymeric material, and dye (with or without a carrier liquid) in the pressure vessel, the vessel was closed and charged with either $CO_2$ or $N_2$ gas. The enclosed system was adjusted to either supercritical or subcritical temperature and pressure conditions for the contained gases (supercritical $CO_2$=31° C. and 7.38 MPa; supercritical $N_2$=−147° C. and 3.39 MPa), and maintained at those conditions for 2 hours, after which the pressure vessel was vented down to ambient conditions. The polymeric materials were recovered from the pressure vessel, rinsed with deionized water, allowed to dry at ambient conditions overnight (e.g. 12–18 hrs.), and were observed to determine the degree of dye impregnation into the polymeric materials, if any. The specific combination of polymer material, impregnation additive, carrier medium (if any), supercritical fluid, including temperature and pressures utilized, method of sample treatment, and observed color change (if any), for Examples 1, and 5–10, and Comparative Examples 2–4, and 11–13 are given in Table 2 below.

After visual observation, each of the dried polymer beads were analyzed using a Minolta Chroma Meter No. CR-200/CR-231 tristimulus color analyzer to determine the degree of rose bengal dye impregnation, if any. Undyed and untreated polymer beads and pellets were utilized as controls. The Chroma Meter is a compact tristimulus color analyzer for measuring reflective colors of surfaces. Absolute measurements were taken in L*a*b, (CIE 1976) in the Munsell color system. For a more in depth review of the measurement parameters of the Chroma Meter color analyzer, reference should be had to the Minolta Chroma Meter CR-200/CR231 Technical Reference Manual, Version 2.0, Minolta, Inc., Japan, the disclosure of which is herein incorporated by reference.

Prior to measuring the reflective color of the beads, the Chroma Meter was color corrected on a standard white plate. Thereafter, control and treated polymer beads were placed in a small plastic weigh boat on the standard white plate in such a way that a layer, two beads thick, could be maintained. The Chroma Meter was placed in intimate contact with the beads and three readings were taken per sample in different locations on the beads. Mean values of L, a and b color space were obtained using the internal statistic capability of the unit.

Color difference between the control and treated beads was calculated as $\Delta E^*_{ab}$ using the following formula:

$$\Delta E^*_{ab} = \sqrt{(\Delta L^*)^2 + (\Delta a^*)^2 + (\Delta b^*)^2}$$

where, L* is the lightness factor (L=0 is black; L=100 is white), and a, and b, are chromaticity coordinates (+a=red; −a=green; +b=yellow; and −b =blue). Total color difference $\Delta E$ is defined by the geometric mean of the differences in the L, a, and b color coordinates between the control and treated polymer beads. The color chromatic coordinates (L, a and b) for the control beads and sample beads of Examples 1, and 5–10, and Comparative Examples 2–4, and 11–13, as well as the color difference ($\Delta E$) between the control and sample beads are shown below in Table 3.

A further analysis was performed on the rose bengal dye-impregnated PE beads of Example 9 to determine the amount of dye incorporated therein. Several grams of these beads were placed in 50 ml deionized water and stirred for 48 hours to extract the dye from the PE beads. A spectroscopic analysis was performed on the dye solution using a Perkin-Elmer, Lambda 4B, uv-vis spectrometer (Perkin-Elmer, Wilton, Conn.) at a wavelength of 356 nm. The results were compared to a standard curve for rose bengal dye. Spectroscopic analysis of the solution confirmed that approximately 0.04 mg of dye per gram of the polyethylene beads had been incorporated into the polyethylene beads during the impregnation process.

TABLE 2

Selected combinations of polymer material, impregnation additive, carrier medium (if any), supercritical fluid, including temperature and pressures utilized, method of sample treatment, and observed color change (if any), for Examples 1 and 5–10, and Comparative Examples 2–4, and 11–13.

| Ex. No. | Polymer Material | Impreg. Additive | Carrier Medium | SC Fluid | Temp (°C.) | Press. (MPa) | Sample Treatment | Observation |
|---|---|---|---|---|---|---|---|---|
| Ex. 1 | PE beads | rose bengal dye | water | $CO_2$ | 60 | 13.8 | PE beads immersed in solution of rose bengal dye and water | PE beads dyed dark pink throughout |
| C. Ex. 2 | PE beads | rose bengal dye | none | $CO_2$ | 60 | 13.8 | PE beads in first vial, dry rose bengal in second vial | PE beads remain milky white in color |
| C. Ex. 3 | PE beads | rose bengal dye | water | $CO_2$ | 60 | 13.8 | PE beads in first vial, sol. of rose bengal and water in second vial | PE beads remain milky white in color |
| C. Ex. 4 | PE beads | rose bengal dye | none | $CO_2$ | 60 | 13.8 | PE beads in vial with dry rose bengal dye | PE beads remain milky white in color |
| Ex. 5 | PP beads | rose bengal dye | water | $CO_2$ | 60 | 13.8 | PP beads immersed in solution of rose bengal and water | PP beads dyed pink throughout |
| Ex. 6 | PA pellets | rose bengal dye | water | $CO_2$ | 60 | 13.8 | PA pellets immersed in solution of rose bengal and water | PE beads dyed light pink throughout |
| Ex. 7 | PE beads | rose bengal dye | ETOH | $CO_2$ | 60 | 13.8 | PE beads immersed in solution of rose bengal and ETOH | PE beads light pink, not in bead center |
| Ex. 8 | PE beads | rose bengal dye | hexane | $CO_2$ | 60 | 13.8 | PE beads immersed in dispersion of rose bengal and hexane | PE beads dyed pink throughout |
| Ex. 9 | PE beads | rose bengal dye | water | $CO_2$ | 35 | 13.8 | PE beads immersed in solution of rose bengal dye | PE beads dyed pink throughout |

TABLE 2-continued

Selected combinations of polymer material, impregnation additive, carrier medium (if any), supercritical fluid, including temperature and pressures utilized, method of sample treatment, and observed color change (if any), for Examples 1 and 5–10, and Comparative Examples 2–4, and 11–13.

| Ex. No. | Polymer Material | Impreg. Additive | Carrier Medium | SC Fluid | Temp (°C.) | Press. (MPa) | Sample Treatment | Observation |
|---|---|---|---|---|---|---|---|---|
| Ex. 10 | PE beads | rose bengal dye | water vapor | $CO_2$ | 60 | 13.8 | PE beads in vial with dry rose bengal, water in bottom of pressure vessel | PE beads remain milky white in color |
| C. Ex. 11 | PE beads | rose bengal dye | water | $CO_2$@ | 60 | 1.3 | PE beads immersed in solution in rose bengal and water | PE beads dyed very light pink |
| C. Ex. 12 | PE beads | rose bengal dye | water | $N_2$@ | 60 | 13.8 | PE beads immersed in solution of rose bengal and water | PE beads remain milky white in color |
| C. Ex. 13 | PE beads | rose bengal dye | ETOH | $CO_2$ | 60 | 13.8 | PE beads in first vial, sol. of rose bengal and ETOH in second vial | PE beads remain milky white in color |

@ 1.3 MPa comprises subcritical pressure conditions for $CO_2$, and 13.8 MPa comprises subcritical pressure conditions for $N_2$.

TABLE 3

Color chromatic coordinates (L, a and b) for the control beads and sample beads of Examples 1, and 5–10, and Comparative Examples 2–4, and 11–13, and color difference ($\Delta E$) between the control and sample beads.

| Controls and Example Nos. | L | a | b | $\Delta E$ |
|---|---|---|---|---|
| Polyethylene Control | 68.82 | −0.52 | +0.84 | |
| Example 1 | 53.52 | +24.22 | −9.58 | 30.90 |
| Comparative Example 2 | 75.58 | +0.73 | −0.97 | 7.10 |
| Comparative Example 3 | 72.95 | +1.66 | −1.61 | 5.27 |
| Comparative Example 4 | 70.28 | +6.90 | −2.84 | 8.41 |
| Polypropylone Control | 70.28 | −1.42 | +6.52 | |
| Example 5 | 53.85 | +18.44 | −3.18 | 27.54 |
| Polyamide Control | 52.74 | −1.14 | +29.35 | |
| Example 6 | 30.16 | +32.22 | +9.56 | 45.10 |
| Example 7 | 68.75 | +3.22 | −1.00 | 4.17 |
| Example 8 | 66.77 | +14.11 | −7.61 | 17.12 |
| Example 9 | na | na | na | na |
| Example 10 | 51.69 | +28.05 | −10.17 | 35.08 |
| Comparative Example 11 | 51.83 | +12.82 | −5.19 | 22.43 |
| Comparative Example 12 | 63.33 | +4.05 | −4.25 | 8.18 |
| Comparative Example 13 | 73.99 | +1.81 | −1.59 | 6.67 |

Comparative examples 2–4 show that rose bengal dye, whether separate or in contact, dry or in solution with water separate from the PE beads, does not impregnate the PE beads, and thus is insoluble in supercritical $CO_2$ at the disclosed conditions. Only by practicing the method of the present invention in Example 1, by simultaneously contacting the PE beads with an aqueous solution of rose bengal dye, is impregnation of the beads accomplished. In addition, Examples 5–9 illustrate that the same or similar results can be achieved with other polymers (PP and PA), other carrier liquids (ETOH and hexane), and at different temperature conditions (Example 1=60° C.; Example 9=35°).

Example 10 shows that impregnation can be accomplished via a carrier liquid in a vapor (e.g., humid $H_2O$) rather than a liquid state. However, in such an instance the degree of visible dye impregnation is considerably lower than that accomplished using the carrier liquid in a liquid state (compare Examples 1 and 10).

Comparative Example 11 shows that some, albeit a significantly lesser degree of dye impregnation, can be accomplished using subcritical $CO_2$ (e.g., 1.3 MPa-v-13.8 MPa). However, use of subcritical $N_2$ does not result in dye impregnation. See Comparative Example 12. Furthermore, Comparative Example 13 confirms the result of Comparative Example 3, except using ETOH versus water as the carrier liquid.

The color measurements provided in Table 3 provide further quantification of the subjective observations of degree of dye impregnation noted in Table 2. Examples 1, 5, 6, and 10 using the preferred method of the present invention show the most pronounced darkening of the sample beads (i.e., reduced L value), the greatest increase in red coloration (greatest+a values), and largest overall color different ($\Delta E$) relative to the control samples. In contrast, the coloration of Comparative Examples 24 show little or no significant difference in coloration from the controls. In this regard, the human eye can at best detect a visible color difference of ±5 units. In addition, the values for Examples 7 and 8 show that ETOH and hexane are not as effective carrier liquids as water (Compare to Example 1).

EXAMPLE 14

Four grams polyamide pellets (No. 19, 105-1, 3 mm diameter, melt index=95° C., Aldrich Chemical Co.) were placed in each of two separate 12 cc glass vials. A blue dye solution of 0.0437 g indigo carmine dye (Aldrich Chemical Co.) in 10 ml deionized water was placed in one vial, and a red dye solution of 0.0755 g rose bengal dye (Aldrich Chemical Co.) in 10 ml deionized water was placed in the second vial. Each vial was covered with a plug of glass wool to maintain the polyamide pellets immersed in the dye solutions. The vials were stacked in a 180 cc MICRO SERIES™ pressure vessel (Newport Scientific Inc.), and the pressure vessel sealed. The vessel was charged with $CO_2$, stabilized at 1.38 MPa and 60° C. and maintained at these conditions for 17 hours. The vessel was slowly vented over a 15 minute period and the sample pellets recovered. Some of the polyamide pellets in the indigo carmine solution were floating, and showed visible blue dye impregnation where they were submerged in the dye solution, and no dye impregnation where they had floated above the dye solution. The polyamide pellets in the rose bengal dye solution remained completely submerged, and showed complete pink dye impregnation. There was no evidence of cross-contamination between the vials containing the dye solutions, as the dye solutions retained their original blue and rose tints, which in turn demonstrated insolubility of the dyes and dye solutions in supercritical $CO_2$ at the indicated temperature and pressure conditions.

The unimpregnated dyes were recovered from the solutions via rotary evaporation (recovered rose bengal dye= 0.0636 g or 84%; recovered indigo carmine dye=0.0380 g or 87%). Thus, the impregnated polyamide pellets contained approximately 16% rose bengal dye, and 13% indigo carmine dye respectively, assuming negligible loss of dye during impregnation.

EXAMPLE 15

Five grams of polyamide pellets (No. 19,105-1; 3 mm diameter; melt index=95° C.; Aldrich Chemical Co.), five grams of polyethylene beads (ASPEN™ No. 6806; 3 mm diameter; melt index=105° C.; linear low density polyethylene, Dow Chemical Co.) and an approximately 2.5 cm×2.5 cm×1 mm thick polyurethane film (source unknown) were placed in a single glass vial containing a dye solution of 50 ml deionized water, 13 mg rose bengal dye (Aldrich Chemical Co.) and 2 drops of an aqueous solution of FD&C blue dye No. 1 (Schilling Food Color; McCormick & Co., Hunt Valley, Md.). A glass wool plug was used to keep the polymer samples submerged in the dye solution. The vial was placed in a 180 cc MICRO SERIES™ pressure vessel, which was sealed, charged with carbon dioxide, stabilized at 50° C. and 13.8 MPa, and maintained for 17 hours. Thereafter, the vessel was vented down over a 1 minute period, and the polymer samples and dye solution recovered. Each of the polymer samples were rinsed with two portions of deionized water and blotted dry. The polyurethane film was removed, and the polyamide pellets and polyethylene beads were separated from one another by shape differentiation. All polymer samples were colored bluish-rose indicating impregnation by both dyes therein.

Each of the three polymer samples were placed in a beaker containing 20 mils of a pH 9 aqueous buffer solution (Fisher Scientific Co., Fairlawn, N.J.), and stirred overnight. Each of the aqueous buffer solutions were qualitatively analyzed in a Perkin-Elmer, Lambda 4B, uv-vis spectrometer (Perkin-Elmer, Wilton, Conn.) at wavelengths of 514 nm and 550 nm. Both the buffer solutions containing the polyamide pellets and the polyethylene beads contained partially extracted dyes, which when analyzed showed absorbencies at 514 nm and 550 nm for the FD&C blue dye No. 1, and rose bengal dye, respectively. The buffer solution containing the polyurethane film sample did not contain any extracted dyes.

EXAMPLE 16

Five grams polyethylene beads (ASPEN™ No. 6806; 3 mm diameter; melt index=105° C.; linear low density polyethylene, Dow Chemical Co.), a 25 cm×25 cm×1 mm thick polyurethane (PU) and polyethylene terephthalate (PET) laminated film (source unknown), and an approximately 3.5 cm×3.5 cm×1 mm thick silicone film (SILASTIC™ No., Dow Corning Corp., Midland, Mich.) were placed in a 25 cc glass vial containing 0.25 g rose bengal dye (Aldrich Chemical Co.) dissolved in 25 mls of absolute ethyl alcohol (ETOH). The vial was placed in a 300 cc pressure vessel. In addition, 30 mils ETOH was also placed in the bottom of the pressure vessel, outside the glass vial, to create a saturated ETOH/supercritical $CO_2$ solution, and thereby prevent the complete uptake of the ethanol from the sample vial, when the pressure vessel was pressurized.

After placement of the vial and excess ETOH, the pressure vessel was closed, charged with $CO_2$, stabilized at 20.7 MPa and 40° C., and maintained for 4 hours. Thereafter, the pressure vessel was vented down over a 2 minute period, and the polymer samples recovered and rinsed with deionized water. The polyethylene beads were pink, and the silicone film was red, indicating impregnation by the rose bengal dye. In addition, the polyurethane side of the PU/PET film was red, indicating dye impregnation, but the PET layer on the opposite side of the film laminate remained clear. Thus, the disclosed impregnations conditions were sufficient to provide impregnation of all but the PET polymer. In this regard, the PET would probably require more rigorous temperature and pressure conditions to provide for impregnation of the rose bengal dye therein.

Comparative Example 17

Two pieces of polyvinyl chloride (PVC) tubing (TYGON™ tubing; Norton Co., Worcester, Mass.), which contain a plasticizing agent were weighed. The first sample weighed 2.0732 grams and was placed in a test tube without water. The second sample weighed 2.1546 grams and was placed in a test tube containing a solution of 0.1050 g of indigo carmine dye (Aldrich Chemical Co.) in 20 ml of deionized water. Both test tubes were placed in a pressure vessel, which was sealed, charged with $CO_2$, stabilized at 20.7 MPa and 50° C., and maintained for 5 hours. Thereafter, the pressure vessel was rapidly vented down to atmospheric pressure, and the samples were recovered.

The first sample of PVC tubing exposed directly to supercritical $CO_2$ foamed, visibly shrank in size, became very stiff, and lost 0.4307 grams, or approximately 20 percent of its total weight. In addition, the test tube containing the first sample also contained a small portion of an oily liquid, assumed to contain extracted plasticizer, based on the stiff physical characteristics of the foamed tubing.

The second sample of PVC tubing immersed in the indigo carmine dye solution retained its soft, pliable character, and foamed due to the rapid venting of the pressure vessel. The final weight of the second sample was 2.0770 grams, a slight increase of 3.8 mg, most likely due to absorption of moisture into the foamed tubing. In addition, none of the oily substance observed with the first sample was observed on the tubing, or in the dye test tube containing the dye solution. Furthermore, no impregnation of the indigo carmine dye was observed in the second sample of foamed tubing.

This example shows that the method of the present invention does not lead to unwanted extraction of additives from the polymer to be impregnated, as is observed when utilizing the prior art method. In addition, while dye impregnation was not accomplished under the disclosed conditions, it may be reasonably assumed that more rigorous temperature and/or pressure conditions could result in the impregnation of indigo carmine dye into the PVC tubing. Furthermore, through more selective control of the venting of the pressure vessel (i.e. more slowly), foaming of the PVC tubing could be prevented.

While in accordance with the patent statutes, description of the preferred weight fractions, and processing conditions have been provided, the scope of the invention is not to be limited thereto or thereby. Various modifications and alterations of the present invention will be apparent to those skilled in the art without departing from the scope and spirit of the present invention.

EXAMPLES 18–23 and

Comparative Example A, B, C, D and E

Determine percent of insulin or trypsin loading and amount of release of insulin or trypsin from crosslinked bovine serum albumin microspheres (BAM).

Preparation of Crosslinked BAM

Bovine serum albumin microspheres (BAM) were made using a procedure similar to that described in U.S. Pat. No. 4,147,767, Example 1, Sample A and such description is incorporated herein by reference. The major differences between the procedure described in U.S. Pat. No. 4,147,767 and the one used in the following examples is (1) the omission of the drug, so that the drug can be impregnated afterward using the process of the present invention and (2) Bovine serum albumin was used instead of human serum albumin.

Bovine serum albumin (BSA) (Sigma Chemical Co., St. Louis, Mo.) was dissolved in water to make a 30 (w/v) % solution. One liter of corn oil (Mazola Corn Oil, Best Foods, CPC International, Inc., Englewood Cliffs, N.J.) was placed in a flat-bottomed beaker (110 mm high by 60 mm in diameter) equipped with four baffles (8 mm depth) positioned against the wall of the beaker. A motor-driven three-blade propeller-type stirrer was placed in the center of the beaker, two-thirds into the oil, so that there was a distance of 23 mm between the baffles and the propeller. A 20 ml syringe with a 26G1/2 hypodermic needle was filled with 15 ml of the BSA solution. The solution was added dropwise to the oil as it was being stirred at 1500 rpm forming a water-in-oil emulsion. While the stirring was continued, the temperature of the oil bath was raised to 115° C. for Example 18 and Comparative Examples A–C, 120° C. for Examples 21, 23 and Comparative Examples D–E, 125° C. for Example 19, and 135° C. for Examples 20 and 22. Cross-linked microspheres were formed by holding the desired temperature of the oil for 1 hour. The oil bath was allowed to cool back to room temperature (25° C.) while stirring at 2000 rpm. The microspheres were filtered from the oil on a 0.25 µm Millipore™ filter (Millipore Corporation, Milford, Mass.) using vacuum filtration. The filtered microspheres were washed three times in 100 ml aliquots of n-heptane and sonicated in a bath sonicator ("Branson Model 2200" from Branson Ultrsonics Corp., Danbury, Conn.) for 30 seconds in 100 ml of n-heptane to avoid any agglomeration and to remove the final traces of oil. The microspheres were filtered from n-heptane as described above for filtering from oil. The residual n-heptane was removed from the microspheres under vacuum. The diameter of the microspheres ranged from 10 to 150 microns, but those microspheres which ranged in size from 25 µm to 52 µm were selected by using a Sonic AutoSiever (Model GA-1) commercially available from Gilson Co., Worthington, Ohio. The pulse amplitude was set at power level 60 with alternate vertical/horizontal tapping. Seives: No. 100 (150 micrometers, µm), No. 120 (125 µm), No. 140 (106 µm), No. 200 (74 µm), No. 230 (63 µm), No. 270 (53 µm), No. 325 (45 µm), No. 400 (38 µm), No. 500 (25 µm) were used to separate the microspheres. Only those microspheres from Seive Nos. 325, 400, and 500 were used in Examples 18–23 and Comparative Examples A, B, D and E. In Comparative Example C, the microspheres ranged from 10–50 µm in diameter.

Impregnating BAM with insulin or trypsin

One hundred milligrams of bovine albumin microspheres (BAM) were placed in a microcentrifuge filter unit (Denville Scientific, Inc., Denville, N.J.) in a 300 cubic centimeter MICRO SERIES™ pressure vessel (29/16 inch outside diameter, 11¾ inch overall length; Newport Scientific, Inc., Jessup, Md.) for Comparative Examples A–E or in a 500 cubic centimeter pressure vessel (316 Stainless Steel (SS) 3¾ inch outside diameter, 7½ inch overall length without the head; Parr Instrument, Moline, Ill.) for Examples 18–23. The BAM were contacted with, or remained separate from, 35 mg of bovine insulin (Sigma Chemical Co., St. Louis, Mo.) or trypsin (Sigma Chemical Co.) in either a dry form or in a solution of 35 mg of bovine insulin in 1 ml of water (pH 4.0) or in a phosphate buffered saline (PBS) solution of trypsin (35 mg/ml, pH 7.4). Example 23 also included 5 microliters of a fluorochemical surfactant (Fluorad Brand fluorochemical surfactant FC-170C from 3M, St. Paul Minn.). After placement of the BAM, and insulin or trypsin (with or without a carrier liquid) in the pressure vessel, the vessel was closed and charged with pure $CO_2$. The enclosed system was adjusted to supercritical temperature and pressure conditions of 8.3 Mpa (1,200 psig) or 13.8 Mpa (2,000 psig) at 35° C. The system was maintained at this condition for 2 hours before slowly venting down to ambient conditions. The microcentrifuge filter units contain a polypropylene microcentrifuge tube with a filter insert having a volume capacity of 3.0 ml. The filter insert that is useful for general filtration of aqueous or organic samples is a microporous nylon membrane filter with a pore size of 0.45 µm. This filter insert was used for removing particulate from the supercritical fluid during the loading process and for preventing microspheres from overflowing during the venting down process after impregnation. The microsphere suspensions were allowed to stand overnight (14–16 hours) at 4° C. to allow complete removal of air bubbles. The suspensions were filtered and both the filtrate (CF) and the microspheres were used to evaluate for insulin or trypsin content. The microspheres were air-dried and stored at −70° C in a low-temperature freezer until tested.

Evaluation of loading efficiency

Twenty-five milligrams of insulin- or trypsin-loaded microspheres were weighed and washed seven times with 50 ml of phosphate buffered saline (PBS) solution at room temperature in 150 ml Corning sterile filter unit with 0.22 µm cellulose acetate membrane. The washes (CA) were saved to analyze for insulin or trypsin content. The microsphere particles were transferred into a glass homogenizing tube and manually homogenized for 5 minutes in 25 ml of 0.1 N HCl in which both insulin and trypsin were readily soluble. The crushed microspheres were sonicated in a bath sonicator ("Branson Model 2200" from Branson Ultrasonics Corp., Danbury, Conn.) for 30 minutes to insure complete solubilization of insulin or trypsin. At the end of sonication, the temperature of the sample was 40°±4° C. The sonicated microsphere preparation was centrifuged and the insulin or trypsin content of the resulting supernatant ($C_R$) was used to evaluate insulin or trypsin content.

The loading efficiency was calculated by the following equation:

$$\text{Percent Drug Load} = (C_A + C_B)/(C_A + C_B + C_F) \times 100$$

where $C_A$ is the concentration of insulin or trypsin in the PBS washes, $C_B$ is the concentration of insulin or trypsin in the supernatant, and $C_F$ is the concentration of insulin or trypsin in the filtrate. These concentrations were determined by high performance liquid chromatography (HPLC) and radio-immuno assay (RIA) for insulin, and spectrometric enzyme activity measurement methods for trypsin. The specific combination of BAM, impregnation additive, carrier medium (if any), supercritical fluid, including temperature and pressures utilized, method of sample treatment, and percent of insulin loading (if any) for Examples 18–20 and Comparative Examples A–C are summarized in Table 4 or percent of trypsin loading (if any) for Examples 21–23 and Comparative Examples D and E are summarized in Table 5.

HPLC Measurements

Analytical determinations of insulin were made using a HPLC method with spectrometric UV determination (214 nm). The apparatus used consisted of an injector (Shimadzu Model Sil-9A, Shimadzu, Columbia, Md.), a solvent delivery system (Waters 625, Millipore Corporation, Milford, Mass.), a variable wavelength detector (Waters 490E, Millipore Corporation) and an integrator (Waters Baseline, Millipore Corporation). The insulin containing solutions were injected into the Beckman Ultrapore reversed phase(RP) C-18 column (7.5 cm, 4.6 mm) attached to a guard column packed with RP C-18. The mobile phase was a gradient mixture of acetonitrile and 0.1% trifluoroacetic acid CFFA) in water. The gradient conditions in terms of acetonitrile content were 20–30% in 25 minutes and 30–45% in 5 minutes at a flow rate of 1.0 ml/min.

RIA Measurements

Low concentration of insulin was measured following RIA procedure using the "Coat-A-Count Kit" (Diagnostic Product Corp., Los Angeles, Calif.). The antibody of insulin was incubated for a day at room temperature with insulin samples or standard dilution of insulin and radiolabelled [$^{125}$I] insulin. The next day, bound [$^{125}$I] insulin was separated by decanting the contents of tubes and counting the remaining [$^{125}$I] insulin for 1 minute in a gamma counter.

Spectrometric Enzyme Activity Measurements

The assays for trypsin activity were performed using a modification of the original kinetic assay described by Kawabata, S., et al. (European Journal of Biochemistry, 172: 17, 1988). The procedure used N-t-boc-Gln-Ala-Arg 7 amido 4-methyl-coumarin (Sigma Chemical Co.) as a substrate. The incubation mixture (volume 1.0 ml) contained 0.95 ml of normal saline and 50 ml of diluted trypsin samples from release experiments. The reaction was initiated by the addition of 200 μl of 1 mM substrate solution. The substrates were added as 10% dimethylformamide solution, the final concentration of solvent in the assay did not exceed 1.7% (v/v). The assays were run in duplicate, and sets containing no enzyme were used to determine the non-enzymatic rate. The increase in fluorescence due to the liberation of fluorescent methyl-coumarin was continuously monitored with a Perkin-Elmer spectro-fluometer for 3 minutes. The excitation wavelength was 370 nm and sample emission was recorded at 460 nm. Amounts of trypsin in the samples were calculated from the standard curves by convening the initial velocities of fluorescence increase into concentrations of trypsin.

TABLE 4

Selected combinations of polymer material, impregnation additive, carrier medium (if any), supercritical fluid, including temperature and pressures utilized, method of sample treatment, and percent of drug loading (if any), for Examples 18–20 and Comparative Examples A, B and C.

| Ex. No. | Polymer Material | Impreg. Additive | Carrier Medium | SC Fluid | Temp (°C.) | Press. (MPa) | Sample Treatment | Drug Load (%) |
|---|---|---|---|---|---|---|---|---|
| Ex. 18 | BAM microspheres X-linked @ 115° C. | insulin | water | $CO_2$ | 35 | 8.3 | BAM immersed in solution of insulin and water | 14.730 |
| C. Ex. A | BAM microspheres X-linked @ 115° C. | insulin | none | $CO_2$ | 35 | 13.8 | BAM in first unit, dry insulin in second unit | 0.000 |
| C. Ex. B | BAM microspheres X-linked @ 115° C. | insulin | none | $CO_2$ | 35 | 13.8 | BAM in unit with dry insulin | 0.475 |
| C. Ex. C | BAM microspheres X-linked @ 115° C. | insulin | none | $CO_2$ | 35 | 8.3 | BAM in unit with dry insulin | 0.400 |
| Ex. 19 | BAM microspheres X-linked @ 125° C. | insulin | water | $CO_2$ | 35 | 8.3 | BAM immersed in solution of insulin and water | 7.659 |
| Ex. 20 | BAM microspheres X-linked @ 135° C. | insulin | water | $CO_2$ | 35 | 8.3 | BAM immersed in solution of insulin and water | 3.201 |

TABLE 5

Selected combinations of polymer material, impregnation additive, carrier medium (if any), supercritical fluid, including temperature and pressures utilized, method of sample treatment, and percent of drug loading (if any), for Examples 21–23 and Comparative Examples D and E.

| Ex. No. | Polymer Material | Impreg. Additive | Carrier Medium | SC Fluid | Temp (°C.) | Press. (MPa) | Sample Treatment | Drug Load (%) |
|---|---|---|---|---|---|---|---|---|
| Ex. 21 | BAM microspheres | trypsin | Phosphate Buffered Saline | $CO_2$ | 35 | 13.8 | BAM immersed in solution of trypsin and PBS | 4.432 |

TABLE 5-continued

Selected combinations of polymer material, impregnation additive, carrier medium (if any), supercritical fluid, including temperature and pressures utilized, method of sample treatment, and percent of drug loading (if any), for Examples 21–23 and Comparative Examples D and E.

| Ex. No. | Polymer Material | Impreg. Additive | Carrier Medium | SC Fluid | Temp (°C.) | Press. (MPa) | Sample Treatment | Drug Load (%) |
|---|---|---|---|---|---|---|---|---|
| | X-linked @ 120° C. | | Solution | | | | | |
| C. Ex. D | BAM microspheres X-linked @ 120° C. | trypsin | none | $CO_2$ | 35 | 13.8 | BAM in first unit, dry trypsin in second unit | 0.000 |
| C. Ex. E | BAM microspheres X-linked @ 120° C. | trypsin | none | $CO_2$ | 35 | 13.8 | BAM in unit with dry trypsin | 0.285 |
| Ex. 22 | BAM microspheres X-linked @ 135° C. | trypsin | Phosphate Buffered Saline Solution | $CO_2$ | 35 | 13.8 | BAM immersed in solution of trypsin and PBS | 1.180 |
| Ex. 23 | BAM microspheres X-linked @ 120° C. | trypsin | Phosphate Buffered Saline Solution | $CO_2$ | 35 | 13.8 | BAM immersed in solution of trypsin, surfactant, and PBS | 10.980 |

Results of impregnation of insulin and trypsin in BAM

Comparative Examples A and D showed that insulin or trypsin, when separate and dry did not impregnate the BAM, and thus were insoluble in supercritical $CO_2$ at the disclosed conditions. Comparative Examples B, C and E showed that insulin or trypsin when in contact and dry slightly impregnated the BAM, but these results were due to surface adsorption of the insulin or trypsin on the BAM. The percent loading was significantly less than that obtained by practicing the method of the present invention in Example 19 or Example 21 by simultaneously contacting the BAM with an aqueous solution of insulin or a PBS of trypsin. In addition, Examples 19, 20, and 22 illustrated that the same or similiar results could be achieved with other conditions of crosslinking the BAM. Example 23 showed that the addition of a fluorochemical surfactant doubles the percent of loading of BAM.

Drug Release Evaluation

In vitro release of insulin or trypsin from the microspheres was monitored using a Wheaton side-arm flask (volume capacity:250 ml) with overhead stirrer. Fifty milligrams of insulin- or trypsin-loaded microspheres were weighed and washed seven times with 50 ml of phosphate buffered saline (PBS, pH 7.4) solution at room temperature in a 150 ml Corning sterile filter unit with 0.22 µm cellulose acetate membrane. The washes were collected to determine insulin or trypsin content. The microspheres were gently scraped off of the filter, placed in the drug release apparatus, and brought into contact with 200 ml PBS solution at pH 7.4 and at room temperature. The buffer solution was magnetically agitated at moderate stirring speed (100 rpm). Aliquots (0.2 ml) were withdrawn at predetermined times over a 60 hour period with a 1 ml syringe from the reservoir through the side arm. The samples were filtered through 0.22 µm Costar syringe filter to exclude any BAM particulate and collected in 1.5 ml tubes. The insulin or trypsin concentration was determined by the methods described above. The results of the drug release study are shown in FIGS. 3 and 4 in terms of cumulative amount of insulin or trypsin in mg.

Results of In vitro release experiments

Figure 3:
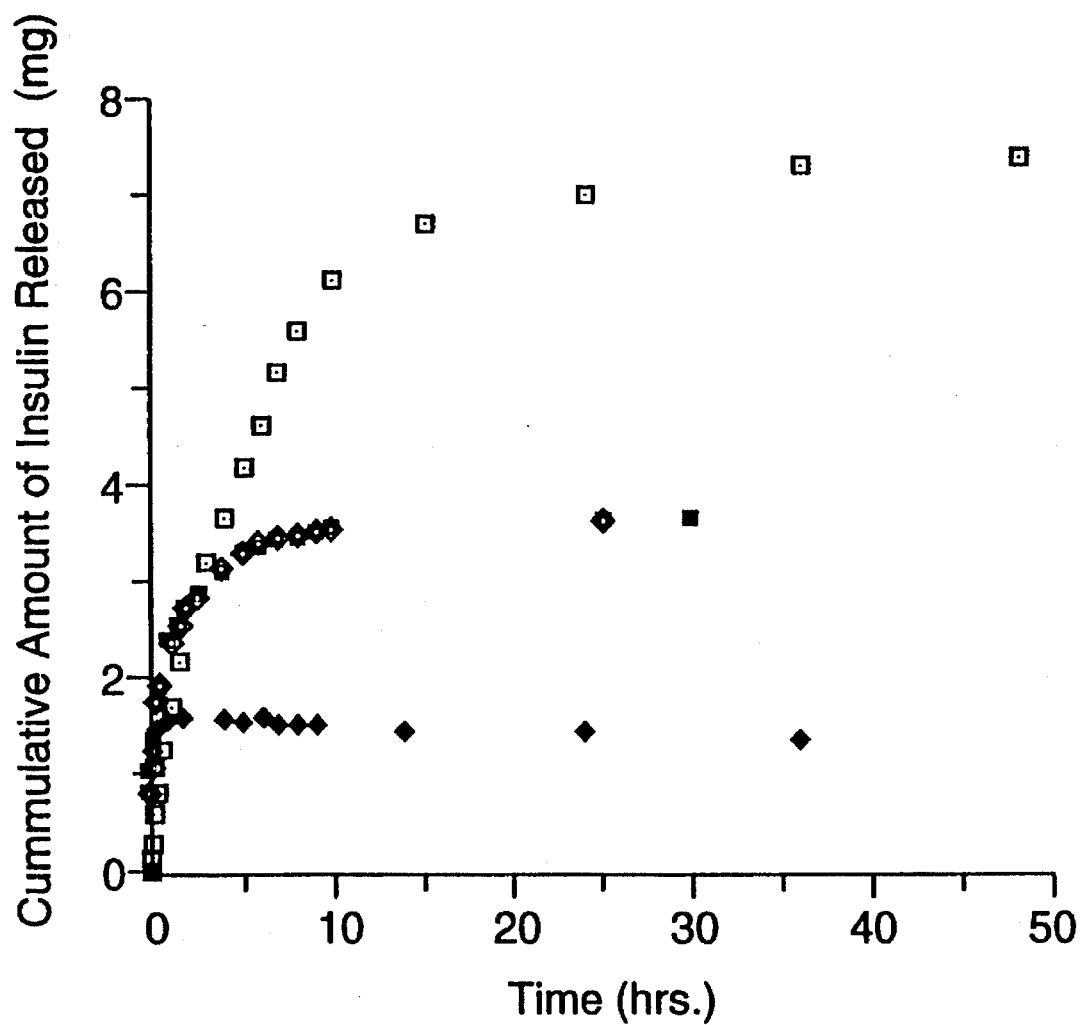
FIG. 3 is a graphical representation of cumulative amount of insulin released (mg) versus time (hrs.).

FIG. 3 showed the effect of crosslinking on the amount of insulin released from BAM. The higher the temperature used to crosslink the BAM, the greater the degree of crosslinking. Higher crosslinking resulted in surface loading instead of core loading, thus the insulin was released slower from Example 18 (less crosslinking) where the BAM was crosslinked at 115° C. than from Examples 19 and 20 (more crosslinking) where the BAM was crosslinked at 125° C. and 135° C., respectively.

Figure 4:
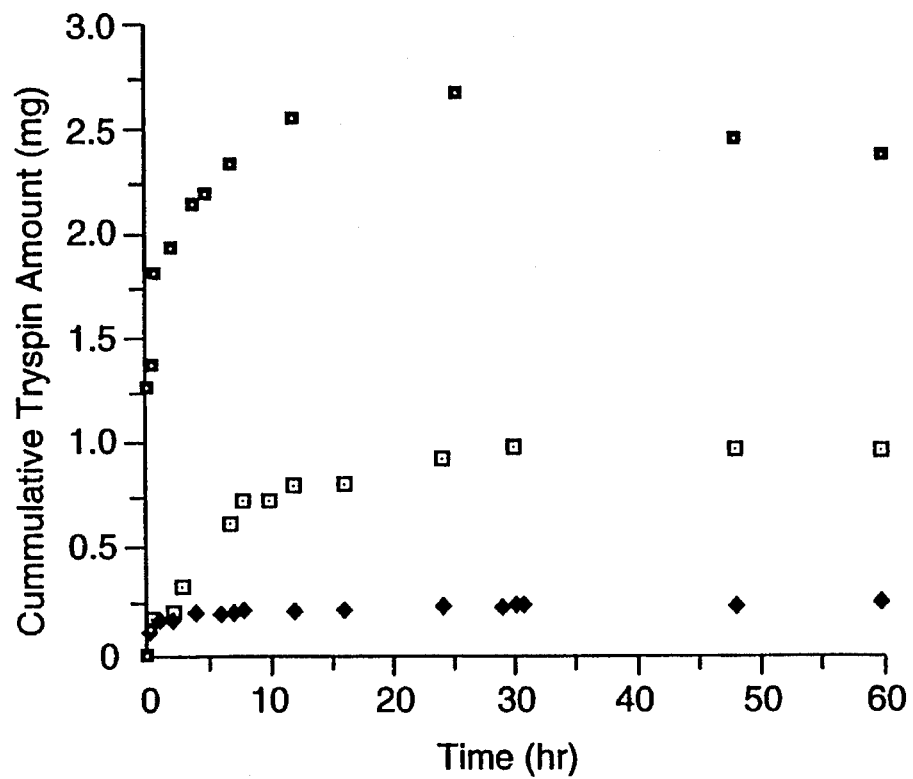
FIG. 4 is a graphical representation of cumulative amount of trypain released (mg) versus time (hrs.).

FIG. 4 showed the effect of adding a surfactant to the carrier medium as well as the effect of crosslinking on the amount of trypsin released from BAM. The BAM in Example 23 were crosslinked at the same temperature as those in Example 21, but the BAM in Example 23 contained a surfactant in the carrier medium with the impregnation additive. The BAM in Example 23 released at nearly the same rate as those in Example 21. The BAM in Example 22 were crosslinked more and released faster than the BAM in Examples 21 or 23.

EXAMPLES 24–26 and

Comparative Examples F–I

Determine the percent of loading of gentamicin.
Preparation of Crosslinked BAM

Bovine serum albumin (BSA) (Sigma Chemical Co., St. Louis, Mo.) was dissolved in water to make a 30 (w/v) % solution. Microspheres were formed by injecting the albumin solution through a 20 gauge hypodermic needle into 800ml of corn oil (Mazola Corn Oil, Best Foods, CPC International, Inc., Englewood Cliffs, N.J.) in a heated bath while stirring at 500–2500 rpm. Stirring rates were measured with a tachometer. The rate of stirring determines to a significant extent the ultimate particle size distribution of the resulting spheres. The average diameter of the microspheres was 10 microns. Stirring was continued while the oil bath temperature was raised from ambient to 115° C. over a 15–30 minute time period. The bath was held at that temperature for from 1 hour. After that time period, the oil bath and its contents were cooled back to room temperature and the resulting microspheres were separated from the oil on Whatman #5 filter paper using vacuum filtration. Final traces of oil were removed from the microspheres by washing them several times with 100–200 ml aliquots of heptane.

The microspheres were air dried and were stored at 4° C. with a desiccant until needed.

Impregnating BAM with gentamicin sulfate

Three concentrations of gentamicin sulfate (Sigma Chemical Co., St. Louis, Mo.) were prepared by dissolving 0.5018, 1.0061, and 2.0076 grams in sterile deionized water to form 10%, 20%, and 40% by weight solutions, respec- 16, 32 and 64 µg/ml; adding the solutions to the seeded agar wells and incubating at 37° C.; plotting a graph of the effect of gentamicin concentration on zone of inhibition size; and calculating a regression line using an exponential curve fitting program. The weight percent of gentamicin loaded in the albumin microspheres for Examples 24–26 and Comparative Examples F–I are given in Table 6.

TABLE 6

Selected combinations of polymer material, impregnation additive, carrier medium (if any), supercritical fluid, including temperature and pressures utilized, method of sample treatment, and percent of drug loading (if any), for Examples 24–26 and Comparative Examples F–I.

| Ex. No. | Polymer Material | Impreg. Additive | Carrier Medium | SC Fluid | Temp (°C.) | Press. (MPa) | Sample Treatment | Drug Load A/B (%) |
|---|---|---|---|---|---|---|---|---|
| Ex. 24 | BAM micro-spheres X-linked @ 115° C. | 40% gentamicin | water | $CO_2$ | 35 | 13.8 | BAM immersed in solution of gentamicin and water | 3.97/2.27 |
| C. Ex. F | BAM micro-spheres X-linked @ 115° C. | gentamicin | none | $CO_2$ | 35 | 13.8 | BAM in first vial, dry gentamicin in second vial | 0.00/0.00 |
| C. Ex. G | BAM micro-spheres X-linked @ 115° C. | gentamicin | none | $CO_2$ | 35 | 13.8 | BAM in vial with dry gentamicin | 0.00/0.00 |
| C. Ex. H | BAM micro-spheres X-linked @ 115° C. | gentamicin | none | $CO_2$ | 60 | 13.8 | BAM in first vial, dry gentamicin in second vial | 0.00/0.00 |
| C. Ex. I | BAM micro-spheres X-linked @ 115° C. | gentamicin | none | $CO_2$ | 60 | 13.8 | BAM in vial with dry gentamicin | 0.17/0.00 |
| Ex. 25 | BAM micro-spheres X-linked @ 115° C. | 20% gentamicin | water | $CO_2$ | 35 | 13.8 | BAM immersed in solution of gentamicin and water | 3.14/2.37 |
| Ex. 26 | BAM micro-spheres X-linked @ 115° C. | 10% gentamicin | water | $CO_2$ | 35 | 13.8 | BAM immersed in solution of gentamicin and water | 2.40/2.71 | tively. Approximately 0.3 g of albumin microspheres were placed in an open vial with 2½ to 3 ml of 10%, 20%, or 40% gentamicin solution. The vial was placed in a 300 cc pressure vessel (Newport Scientific, Inc., Jessup, Md.) which was charged with $CO_2$ and adjusted to 13.8 Megapascal(Mpa) (2,000 psi) at 35° C. The system was maintained at this condition for 4 hours before venting down to ambient pressure. The microspheres were recovered from each vial and rinsed in 500 ml distilled water. Samples were rinsed with 100ml of heptane and air dried.

Procedure A

Ten milligrams of microspheres were suspended in 1 ml of phosphate buffered saline (PBS) solution (pH 7.0) and incubated at ambient temperature for 48 hours on a tube rotator.

Procedure B

Ten milligrams of gentamicin loaded BAM microspheres were dissolved in 1 ml of 2N HCl:ethanol:methanol (1:0.95:1) for 2 hours at 55° C. The solution was diluted 1:100 with phosphate buffered saline (PBS), pH 7.0. The buffered solution was assayed for gentamicin.

Biological gentamicin assay

*Bacillus subtilis*, commercially available as "ATCC 6633" from American Type Culture Collection, Rockville, Md., was grown in trypticase soybroth (TSB) to an optical density of 20 Klett Units/Red Filter (540–700 nm) measured using a Klett-Summersen Spectrophotometer, Klett Manufacturing Co., New York, N.Y. The culture was diluted 1:10 in TSB. The diluted culture (2.5 ml) was added to 500 ml molten trypticase soy agar (TSA) to obtain a population of $5 \times 10^5$ *Bacillus subtilis* cells per ml. The seeded agar was poured into petri dishes to a depth of 3–4 mm. The PBS/gentamicin-albumin solution was placed in 4 mm diameter wells punched in the agar. The petri dishes were incubated right side up at 37° C. Zones of inhibition, which are the clear zones surrounding the wells, were measured and the gentamicin concentration was calculated from a standard curve obtained by making gentamicin solutions of 2, 4, 8, Results of impregnation of gentamicin in BAM Comparative Examples F–I showed that gentamicin, when separate or in contact and dry did not impregnate the BAM, and thus were insoluble in supercritical $CO_2$ at the disclosed conditions. Comparative Example I showed that gentamicin when in contact and dry slightly impregnated the BAM when evaluated using Procedure A, but these results were due to surface adsorption of the gentamicin on the BAM. The percent loading was significantly less than that obtained by practicing the method of the present invention in Examples 24–26 by simultaneously contacting the BAM with an aqueous solution of gentamicin. In addition, Examples 24–26 illustrated that the same or similar results were achieved with different concentrations of gentamicin in the carrier medium.

EXAMPLE 27

Determine core loading and rate of release of insulin in albumin microspheres.

Preparation of Crosslinked BAM

Bovine serum albumin (BSA) (Sigma Chemical Co., St. Louis, Mo.) was dissolved in water to make a 30 (w/v) % solution. Microspheres were formed by injecting the albumin solution through a 16½ or 18½ gauge hypodermic needle into 800 ml of corn oil (Mazola Corn Oil, Best Foods, CPC International, Inc., Englewood Cliffs, N.J.) in a heated bath while stirring at 1000 rpm. Stirring rates were measured with a tachometer. The diameter of the microspheres ranged from 10 to 50 microns as determined by scanning electron microscope. Stirring was continued while the oil bath temperature was raised from ambient to 110° C. over a 15–30 minute time period. The bath was held at that temperature for approximately 1 hour. After that time period, the oil bath and its contents were cooled back to 15° C. and the resulting microspheres were separated from the oil on Whatman #5 filter paper using vacuum filtration. Final traces of oil were removed from the microspheres by washing them several times with 60 ml aliquots of heptane. The microspheres were lyophilized at −50° C. for 24 hours, air dried and stored at 4° C. with a desiccant until needed.

Impregnating BAM with insulin

Bovine albumin microspheres (BAM)(300 mg) were added to 2 ml of an aqueous solution of bovine insulin (15 mg/ml) (Sigma Chemical Co., St. Louis, Mo.) in a microcentrifuge tube. The specific activity of insulin was 24.4 IU/mg. The tube was placed in a 300 cc pressure vessel which was charged with $CO_2$ and adjusted to 8.3 Mpa (1,200 psi) at 35° C. The system was maintained at this condition for 2 hours before venting down to ambient pressure. The microsphere suspension was allowed to stand overnight (14–16 hours) at 4° C. to allow complete removal of air bubbles. The suspension was filtered and the filtrate and the microspheres were evaluated for insulin content. The microspheres were air-dried and stored at −70° C. in a low-temperature freezer until tested for insulin release.

Evaluation of loading efficiency

Twenty milligrams of insulin-loaded microspheres were weighed and washed seven times with 50 ml of phosphate buffered saline (PBS) solution at room temperature in 150 ml Corning sterile filter unit with 0.22 μm cellulose acetate membrane. The washes were saved to analyze for insulin content. The microsphere particles were transferred into a glass homogenizing tube and manually homogenized for 5 minutes in 28 ml of 0.1N HCl in which the insulin was easily soluble. The crushed microspheres were sonicated in a bath sonicator ("Branson Model 2200" from Branson Ultrasonics Corp., Danbury, Conn.) for 1 hour to insure a complete solubilization of insulin. At the end of sonication, the temperature of the sample was 44° C. Insulin concentration was measured by high performance liquid chromatography (HPLC) or radio-immuno assay (RIA) on the supernatant obtained after centrifugation.

RIA Measurements

Insulin was measured following RIA procedure using the "Coat-A-Count Kit" commercially available from Diagnostic Product Corp., Los Angeles, Calif. The antibody of insulin was incubated for a day at room temperature with insulin samples or standard dilution of insulin and radiolabelled [$^{125}$I] insulin. The next 5 day, bound [$^{125}$I] insulin was separated by decanting the contents of tubes and counted for 1 minute in a gamma counter.

HPLC Measurements

Analytical determinations of insulin were made using a HPLC method with spectrometric UV determination (214 nm). The apparatus used consisted of an injector (Shimadzu Model Sil-9A, Shimadzu, Columbia, Md.), a solvent delivery system (Waters 625, Millipore Corporation, Milford, Mass.), a variable wavelength detector (Waters 490E, Millipore Corporation, Milford, Mass.) and an integrator (Waters Baseline, Millipore Corporation, Milford, Mass.). The insulin containing solutions were injected into the Vydac reversed phase (RP) C-18 column (25 cm, 4.6 mm) attached to a guard column packed with RP C-18. The mobile phase was a gradient mixture of acetonitrile and 0.1% trifluoroacetic acid (TFA) in water. The gradient conditions in terms of percent acetonitrile were 5–34% in 30 minutes, 34–36% in 6 minutes, and 36–46% in 8 minutes at a flow rate of 1.0 ml/min.

TABLE 7

Calculation of insulin loading efficiency:

|  | RIA (IU) | HPLC (mg) |
|---|---|---|
| Free insulin after loading (F) | 16.0 | 1.7 |
| Insulin in washing solution from BAMs (Br) | 1.6 | 0.27 |
| Insulin from crushed BAMs (Bc) | 0.031 | 0.0073 |
| Total insulin (T) = F + Br + Bc | 17.6 | 1.98 |
| Loading efficiency (%) = (Br + Bc)/T × 100 | 9.27 | 14.0 |

Drug Release Evaluation

Figure 5:
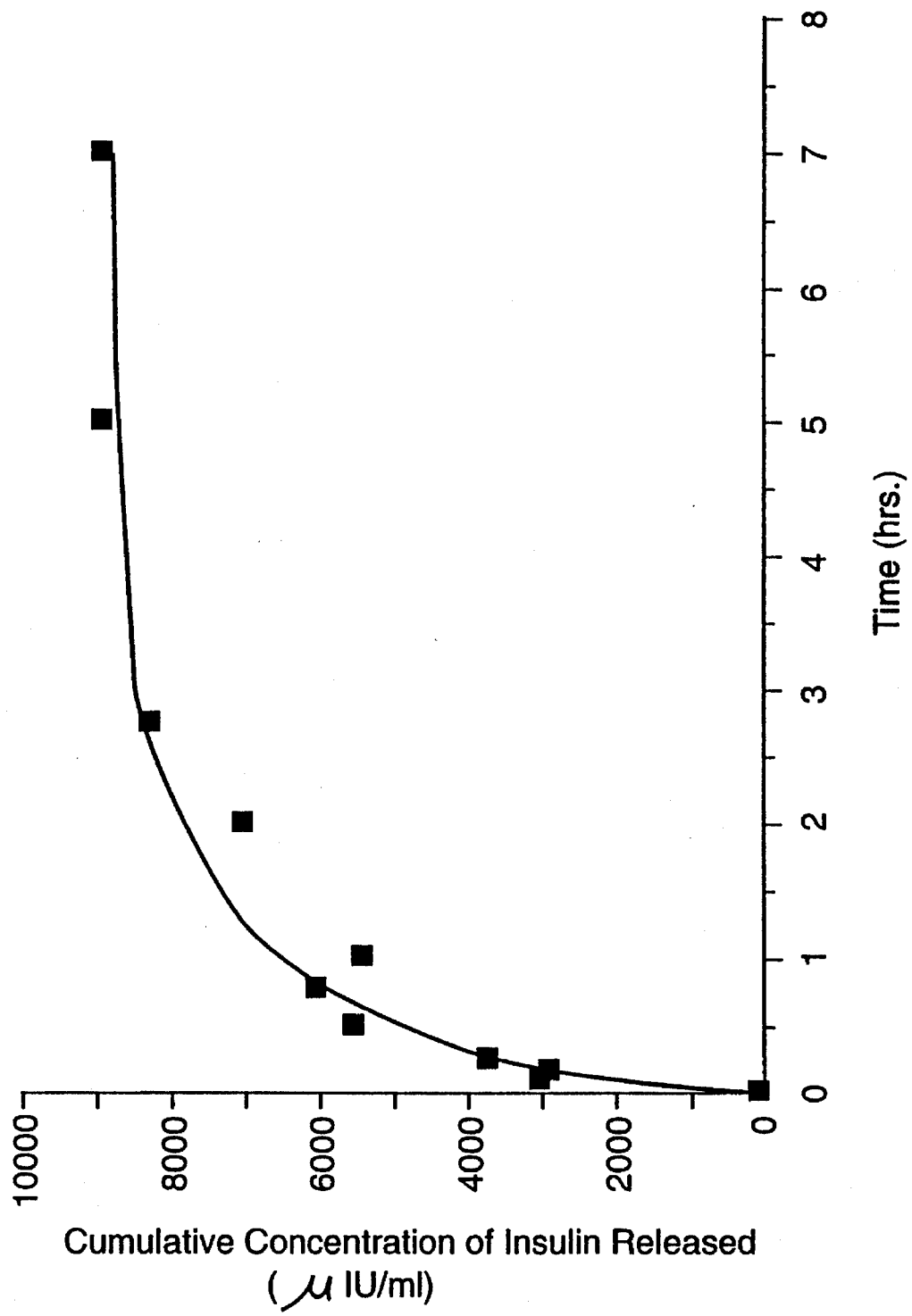
FIG. 5 is a graphical representation of cumulative concentration of insulin released (μIU/ml) versus time (hrs.).

In vitro release of insulin from the microspheres was monitored using a Wheaton side-arm flask with overhead stir. Twenty milligrams of insulin-loaded microspheres were weighed and washed seven times with 50 ml of phosphate buffered saline (PBS) solution at room temperature in a 150 ml Corning sterile filter unit with 0.22 μm cellulose acetate membrane. The washes were collected to determine insulin content. The microspheres were gently scraped off of the filter, placed in the drug release apparatus, and brought into contact with 200 ml PBS solution at pH 7.4 and at room temperature. The buffer solution was magnetically agitated at moderate stirring speed. Aliquots (200 μl) were withdrawn at predetermined times over a 6 hour period with a 1 ml syringe from the reservoir through the side arm. The samples were filtered through 0.22 μm Costar filter to exclude any BAM particulate and collected in 12×75 mm polypropylene tubes. The insulin concentration was determined by RIA methods. The results of the drug release study are shown in FIG. 5 in terms of international unit (IU).

Insulin was measured to be increasingly released from 5 minutes to 6 hours where a maximal release of 8020 μIU/ml was reached at 6 hours. No further increase was detected after 24 hours.

EXAMPLES 38–36

Determine the effect of crosslinking BAM on gentamicin loading.

Preparation of crosslinked BAM

Bovine serum albumin (BSA) (Sigma Chemical Co., St. Louis, Mo.) was dissolved in water to make a 30 (w/v) % solution. Microspheres were formed by injecting the albumin solution through a 20–25 gauge hypodermic needle into 500–800 ml of corn oil (Mazola Corn Oil, Best Foods, CPC International, Inc., Englewood Cliffs, N.J.) in a heated bath while stirring at 500–2500 rpm. Stirring rates were measured with a tachometer. The rate of stirring determines to a significant extent the ultimate particle size distribution of the resulting spheres. The average diameter of the microspheres was 10 microns. Stirring was continued while the oil bath temperature was raised from ambient to 115°–165° C. over a 15–30 minute time period. The bath was held at that temperature for 1–6 hours. Increasing time and temperature increased the degree of crosslinking in the microspheres. After that time period, the oil bath and its contents were cooled back to room temperature and the resulting microspheres were separated from the oil on Whatman #5 filter paper using vacuum filtration. Final traces of oil were removed from the microspheres by washing them several times with 100–200 ml aliquots of heptane. The microspheres were air dried and were stored at 4° C. with a desiccant until needed.

Impregnating BAM with gentamicin sulfate

Two concentrations of gentamicin sulfate (Sigma Chemical Co., St. Louis, Mo.) were prepared by dissolving 1.0061, and 2.0076 grams in sterile deionized water to form 20% and 40% by weight solutions, respectively. A 50 (w/v) % solution of gentamicin was made by dissolving 0.5 g gentamicin sulfate per ml sterile deionized water. Approximately 0.3 g (the exact amount for each example is given in Table 3) of albumin microspheres were placed in an open vial with 2½ to 3 ml of 20%, 40% or 50% gentamicin solution. The vial was placed in a 300 cc pressure vessel commercially available from Newport Scientific, Inc., Jessup, Md. which was charged with $CO_2$ and adjusted to 13.8 Megapascal(Mpa) (2,000 psi) at 35° C. The system was maintained at this condition for 4 hours before venting down to ambient pressure. The microspheres were recovered and rinsed in sterile deionized water. The microspheres were air dried overnight at room temperature and stored at 4° C. with a desiccant until evaluated for core loading and/or drug release.

Procedure for evaluating core loading

Ten milligrams of gentamicin loaded albumin microspheres were dissolved in 1 ml of 2N HCl:ethanol:methanol (1:0.95:1) for 20 minutes at 55° C. The solution was diluted 1:100 with phosphate buffered saline (PBS), pH 7.0. The buffered solution was assayed for gentamicin.

Gentamicin Biological Assay

Bacillus subtilis, ("ATCC 6633" from American Type Culture Collection, Rockville, Md.) was grown in trypticase soybroth (TSB) to an optical density of 20 Klett Units/Red Filter (540–700 nm) measured using a Klett-Summersen Spectrophotometer, Klett Manufacturing Co., New York, N.Y. The culture was diluted 1:10 in TSB. The diluted culture (2.5ml) was added to 500 ml molten trypticase soy agar (TSA) to obtain a population of $5 \times 10^5$ Bacillus subtilis cells per ml. The seeded agar was poured into petri dishes to a depth of 3–4 mm. The PBS/gentamicin-albumin solution was placed in 4 mm diameter wells punched in the agar. The petri dishes were incubated right side up at 37° C. Zones of inhibition, which are the clear zones surrounding the wells, were measured and the gentamicin concentration was calculated from a standard curve obtained by making gentamicin solutions of 2, 4, 8, 16, 32 and 64 μg/ml; adding the solutions to the seeded agar wells and incubating at 37° C.; plotting a graph of the effect of gentamicin concentration on zone of inhibition size; and calculating a regression line using an exponential curve fitting program. The weight percent of gentamicin loaded in the albumin microspheres for Examples 38–36 is reported in Table 8.

Procedure for Evaluating Drug Release

Figure 6:
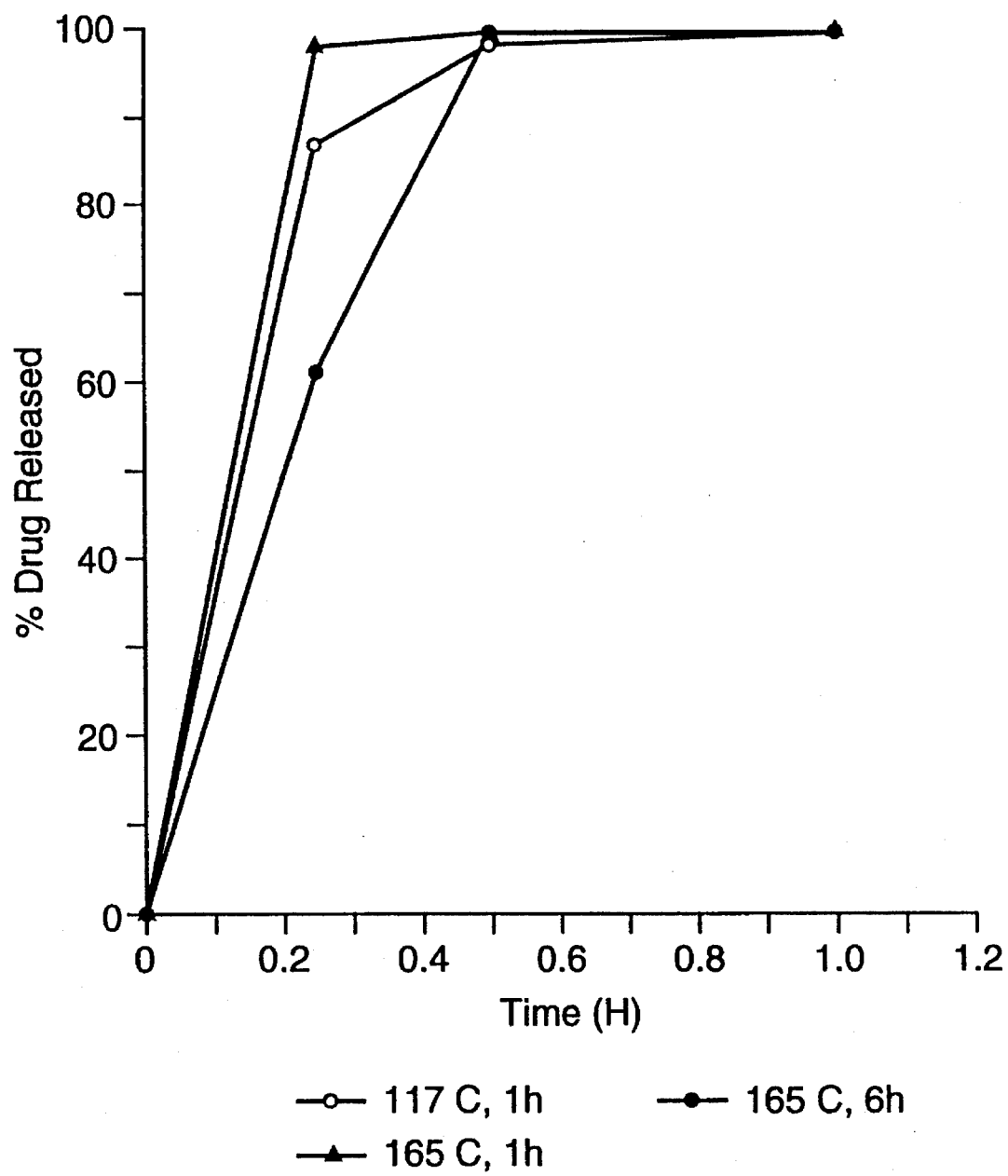
FIG. 6 is a graphical representation of % drug released versus time (hrs.) of the effect of degree of cross-linking on release rates.

Examples 33–36 were evaluated for drug release using the following procedure: 10 milligrams of gentamicin loaded albumin microspheres were suspended in 1 ml of PBS in a microcentrifuge tube. The tubes were incubated on a 5 tube rotator (Scientific Equipment Products, Baltimore, Md.) at room temperature. After ¼ hour the tubes were centrifuged for 3–5 minutes in a Fisher Model 235C microcentrifuge (Fisher Scientific, Pittsburgh, Pa.). The supernatants were removed and stored at 4° C. until assayed by the gentamicin biological assay described above. The microspheres were resuspended in 1 ml of fresh PBS and returned to the rotator for the next time point. Total time points were ¼, ½ and 1 hour. The drug release rate for Examples 32, 34, and 35 is shown in FIG. 6.

Figure 7:
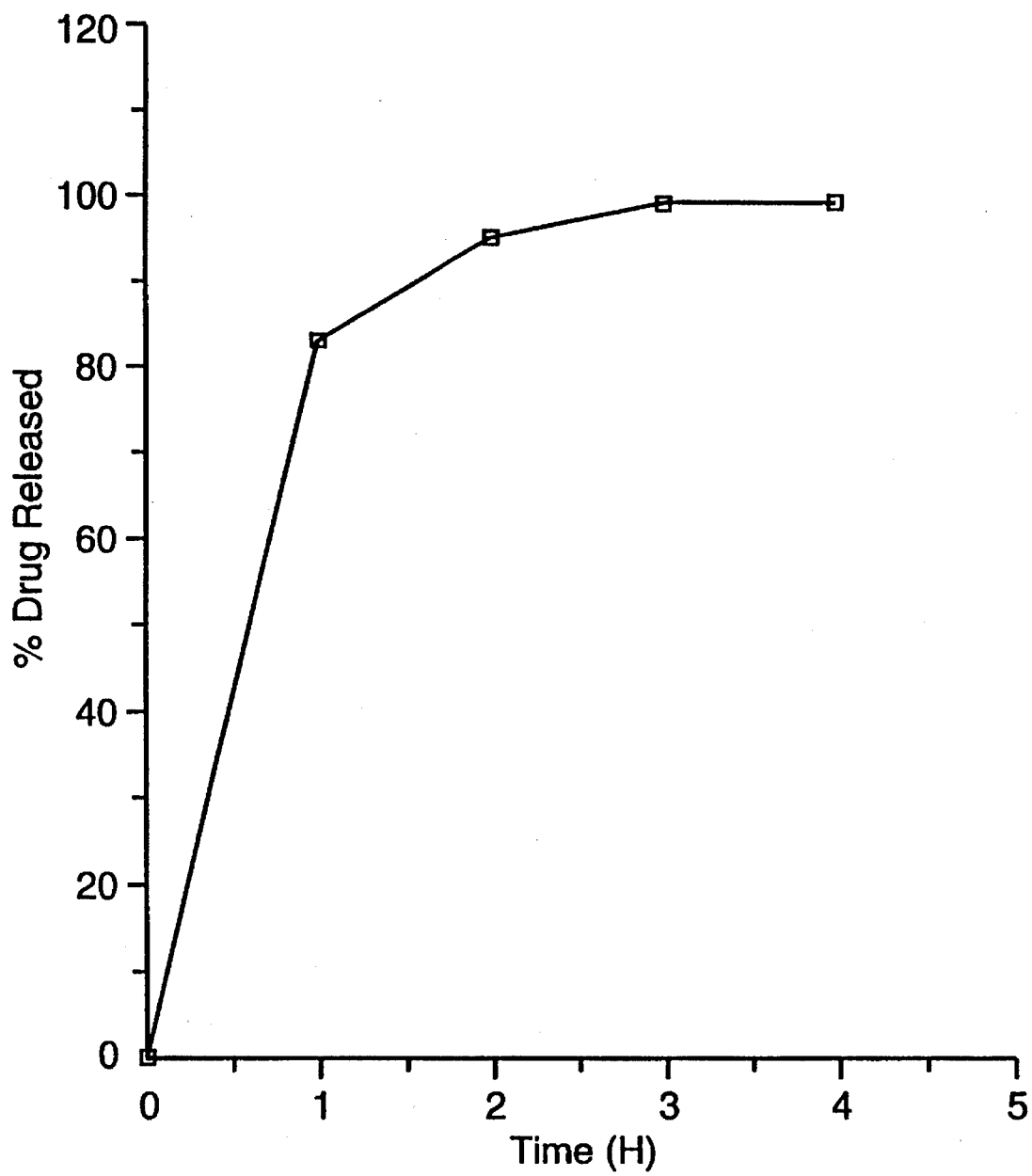
FIG. 7 is a graphical representation of % drug released versus time (hrs.) of gentamicin from albumin microspheres.

Example 28 was evaluated for drug release using the following procedure. Ten milligrams of gentamicin loaded albumin microspheres were suspended in 10 ml of PBS in a microcentrifuge tube. The tubes were agitated gently at room temperature. At 1, 2, 3, and 4 hour intervals 0.5 ml aliquots were removed, and were centrifuged for 3–5 minutes to pellet the microspheres in a Fisher Model 235C microcentrifuge (Fisher Scientific, Pittsburgh, Pa.). The supernatants were removed and stored at 4° C. until assayed by the gentamicin biological assay described above. The drug release rate for Example 28 is shown in FIG. 7.

TABLE 8

Effect of crosslinking albumin microspheres on gentamicin loading

| Example | Concentration of gentamicin sulfate (%) | Amount of albumin microspheres (g) | Crosslinking Conditions Temperature (°C.) | Time (hr) | Core Loading (wt. %) |
|---|---|---|---|---|---|
| 28 | 50 |  | 115 | 1 | 13.2 |
| 29 | 40 | 0.2060 | 117 | 1 | 16.9 |
| 30 | 40 | 0.3017 | 140 | 6 | 14.4 |
| 31 | 40 | 0.3086 | 165 | 1 | 25.0 |
| 32 | 40 | 0.3065 | 165 | 6 | 3.0 |
| 33 | 20 | 0.3328 | 117 | 1 | 17.0 |
| 34 | 20 | 0.2043 | 140 | 6 | 3.0 |
| 35 | 20 | 0.3035 | 165 | 1 | 11.0 |
| 36 | 20 | 0.2717 | 165 | 6 | 3.0 |

The results demonstrated that the less crosslinking in the microspheres, the greater the amount of core loading regardless of the concentration of the gentamicin.

EXAMPLES 37–41

Variable loading of polymers as a function of particle size and concentration of additive.

Three concentrations of gentamicin sulfate (Sigma Chemical Co., St. Louis, Mo.) were prepared by dissolving 0.5018, 1.0061, and 2.0076 grams in sterile deionized water to form 10%, 20%, and 40% by weight solutions, respectively. The albumin microspheres were made as described for Examples 38–36 except the temperature of the oil bath was 115° C. and the amount of time the temperature was held was for 1 hr. The polyglycolic acid/polylactic acid (PGA/PLA), 50/50, microspheres were obtained as "DuPont Medisorb Microspheres" from Medisorb Technologies International L.P., Cincinnati, Ohio Table 9 shows the amount, particle size and type of microsphere placed in each individual open vial with 2½ to 3 ml of the gentamicin solution. The vials were placed in the 300 cc pressure vessel which was charged with $CO_2$ and adjusted to 13.8 MPa (2,000 psi) at 35° C. These conditions were maintained for 4 hours and then the vessel was slowly returned to ambient conditions over several minutes. The vials were removed, the samples recovered and the excess gentamicin solution was removed by vacuum filtration. The microspheres were quickly rinsed with 2 mls of sterile deionized water and dried in a desiccator overnight. The microspheres were stored at 4° C. with a desiccant until evaluated for core loading using the procedure described for Examples 38–36. The results are shown in Table 9 for Examples 37–41. The PGA/PLA microspheres (Examples 37–38) foamed which may explain the lower percent of core loading for this substrate. The effect of gentamicin concentration on weight percent core loading of albumin microspheres was demonstrated in Examples 39–41. The higher the concentration the greater the amount of loading. These microspheres were less crosslinked than the ones used in Examples 38–36.

TABLE 9

Effect of additive concentration and particle size on core loading

| Example | Concentration of gentamicin sulfate (%) | Amount of PGA/PLA* microspheres (g) | Particle Size (μ) | Amount of albumin microspheres (g) | Core Loading (wt. %) |
|---|---|---|---|---|---|
| 37 | 10 | 0.3015 | 56 | | 0.61 |
| 38 | 10 | 0.3017 | 36 | | 0.41 |
| 39 | 10 | | | 0.3080 | 2.50 |
| 40 | 20 | | | 0.3022 | 6.65 |
| 41 | 40 | | | 0.3058 | 27.00 |

*PGA/PLA = polyglycolic acid/polylactic acid, 50/50, available as "DuPont Medisorb Microspheres" from Medisorb Technologies International L.P., Cincinnati, OH.

EXAMPLES 42–49

Determine the effect of particle size and gentamicin concentration on core loading of polylactic acid microspheres.

High molecular weight polylactic acid (PLA) was purchased as a powder or granules from CCA Biochem, Gorinchem, Holland, and converted to various size microspheres.
Impregnating PLA microspheres with gentamicin sulfate Two concentrations of gentamicin sulfate (Sigma Chemical Co., St. Louis, Mo.) were prepared by dissolving 1.0061, and 2.0076 grams in sterile deionized water to form 20% and 40% by weight solutions, respectively. Approximately 0.3 g of PLA microspheres were placed in an open vial with 2½ to 3 ml of 20% or 40% gentamicin solution. The vial was placed in a 300 cc pressure vessel commercially available from Newport Scientific, Inc., Jessup, Md. which was charged with $CO_2$ and adjusted to 13.8 Megapascal(Mpa) (2,000 psi) at 35° C. The system was maintained at this condition for 3 hours before venting down to ambient pressure. The microspheres were recovered and rinsed in deionized water. The microspheres were air dried overnight at room temperature and stored at 4° C. until evaluated for core loading.
Procedure for core loading Ten milligrams of gentamicin loaded PLA microspheres were dissolved in 1 ml of methylene chloride overnight at room temperature (25° C.). Gentamicin was extracted into 3 ml of distilled water and the extract was stored at 4° C. until used for determining the weight percent of gentamicin by using the gentamicin biological assay described in Examples 38–36. The weight percent of gentamicin loaded in the PLA microspheres for Examples 42–49 is reported in Table 10.

TABLE 10

Effect of additive concentration and particle size on core loading

| Example | Concentration of gentamicin sulfate (%) | Amount of PLA* microspheres (g) | Particle Size (μm) | Core Loading (wt. %) |
|---|---|---|---|---|
| 42 | 20 | 0.3050 | >212 | 1.68 |
| 43 | 20 | 0.3105 | 75–212 | 1.41 |
| 44 | 20 | 0.3080 | 35–75 | 3.11 |
| 45 | 20 | 0.2195 | <35 | 2.88 |
| 46 | 40 | 0.3167 | >212 | 3.89 |
| 47 | 40 | 0.3007 | 75–212 | 3.09 |
| 48 | 40 | 0.3097 | 35–75 | 3.63 |
| 49 | 40 | 0.2090 | <35 | 4.33 |

*PLA = polylactic acid

The greater the concentration of gentamicin and the smaller the particle size of the microsphere, the more weight percent of loading of the PLA microspheres was observed.

EXAMPLES 50–52

Various impregnation conditions were used to load PLA microspheres.

Figure 8:
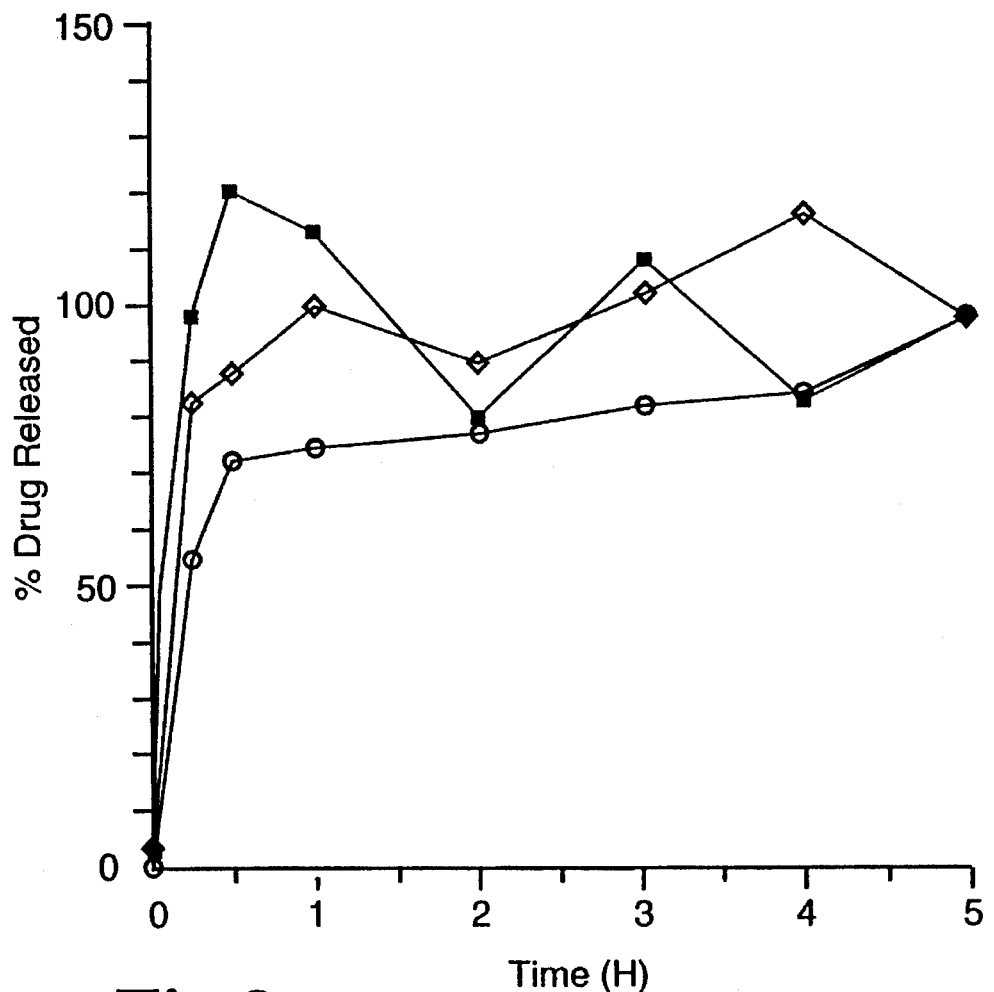
FIG. 8 is a graphical representation of % drug released versus time (hrs.) of the effect of SCF conditions on drug release.

High molecular weight polylactic acid (PLA) was purchased as powder or granules from CCA Biochem, Gorinchem, Holland, and converted to various size microspheres. Impregnating PLA microspheres with gentamicin A concentration of gentamicin sulfate commercially available from Sigma Chemical Co., was prepared by dissolving 2.0076 grams in sterile deionized water to form a 40% by weight solution. Approximately 0.3 g of PLA microspheres were placed in an open vial with 2½ to 3 ml of 40% gentamicin solution. The vial was placed in a 300 cc pressure vessel (Newport Scientific, Inc., Jessup, Md.)which was charged with $CO_2$ or $N_2O$ and adjusted to 13.8 Megapascal(Mpa) (2,000 psi) at 35° C. or 60° C. The system was maintained at this condition for 3 hours or overnight (14–16 hours) before venting down to ambient pressure. The microspheres were recovered and rinsed in sterile deionized water. The microspheres were air dried overnight at room temperature and stored at 4° C. until evaluated for core loading and drug release.
Procedure for Core Loading and Drug Release 100 mg of gentamicin loaded PLA microspheres were suspended in 50 ml of PBS and incubated with gentle agitation at 37° C. 0.5 ml of the suspension were removed at ¼, ½, 1, 2, 3, 4, and 5 hour timepoints and filtered through a 0.45micron cellulose acetate filter to remove the microspheres. Filtrates were stored at 4° C. until evaluated using the gentamicin biological assay described for Examples 38–36. The specific loading conditions and the weight percent core loading are shown in Table 11. The results of the drug release for Examples 50–52 are shown in FIG. 8.

TABLE 11

Effect of Supercritical Conditions on Loading of Gentamicin into PLA Microspheres.

| Example | SCF | Temperature (°C.) | Pressure (Mpa) | Time (hr) | Core Loading (wt. %) |
|---|---|---|---|---|---|
| 50 | $CO_2$ | 60 | 13.8 | 3 | 10.15 |
| 51 | $CO_2$ | 35 | 13.8 | overnight | 9.90 |
| 52 | $N_2O$ | 35 | 13.8 | 3 | 17.10 |

The results demonstrated that increasing temperature or time increased the weight percent core loading if compared to Example 46 in Table 10. The use of nitrous oxide doubled the weight percent core loading in PLA microspheres. The biphasic drug release curves are shown in FIG. 8. There was an initial burst where in over 50% of the gentamicin was released at the first timepoint, and then little but consistent release for about 5 hours. Example 50 showed the best results with Example 51 showing sustained release also.

EXAMPLE 53

Figure 9:
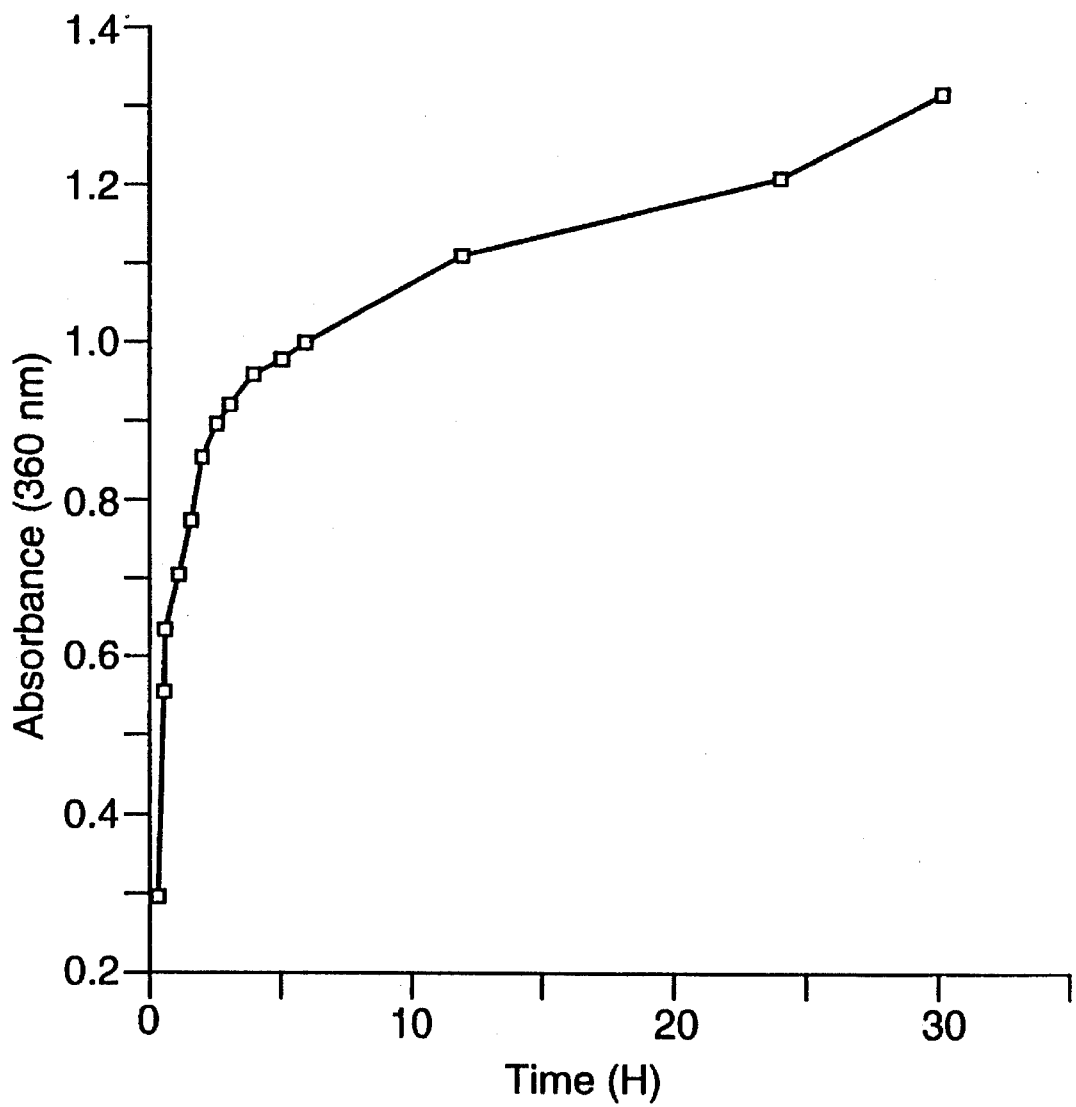
FIG. 9 is a graphical representation of absorbence (360 nm) versus time (hrs.).

Rate of drug release of tetracycline from albumin microspheres.
Preparation of crosslinked BAM
Albumin microspheres were made as described in Examples 38–36 except the temperature of the oil bath was 117° C. and the temperature was held for 1 hr.
Impregnation of BAM with tetracycline
Approximately 0.3 g of BAM were placed in an open vial with 2½ to 3 ml of tetracycline (Sigma Chemical Co.) saturated water (5 g/20 ml deionized water). The vial was placed in a 300 cc pressure vessel (Newport Scientific, Inc., Jessup, Md.)which was charged with $CO_2$ and adjusted to 13.8 Megapascal(Mpa) (2,000 psi) at 35° C. The system was maintained at this condition for 4 hours before venting down to ambient pressure. The microspheres were recovered and rinsed in sterile deionized water. The microspheres were air dried overnight at room temperature and stored at 4° C. until evaluated for drug release.
Procedure for evaluation of drug release
Tetracycline loaded albumin microspheres (200 mg) were added to 10 ml of PBS, pH 6.2, in a centrifuge tube. The tube was incubated at room temperature on a hematology mixer. At time intervals of 10, 20, 30, 60, 90, 120, 150, 180, 240, 300, 360, 720, 1440, and 1820 minutes, the tube was centrifuged at 500 rpm for 5 minutes and the supernatant evaluated by determining the absorbance at 360 nm in a Beckman spectrophotometer. FIG. 9 shows the result of this measurement. The supernatant fluid was replaced in the centrifuge tube and reincubated until time for the next measurement.

EXAMPLES 54–58

Figure 10:
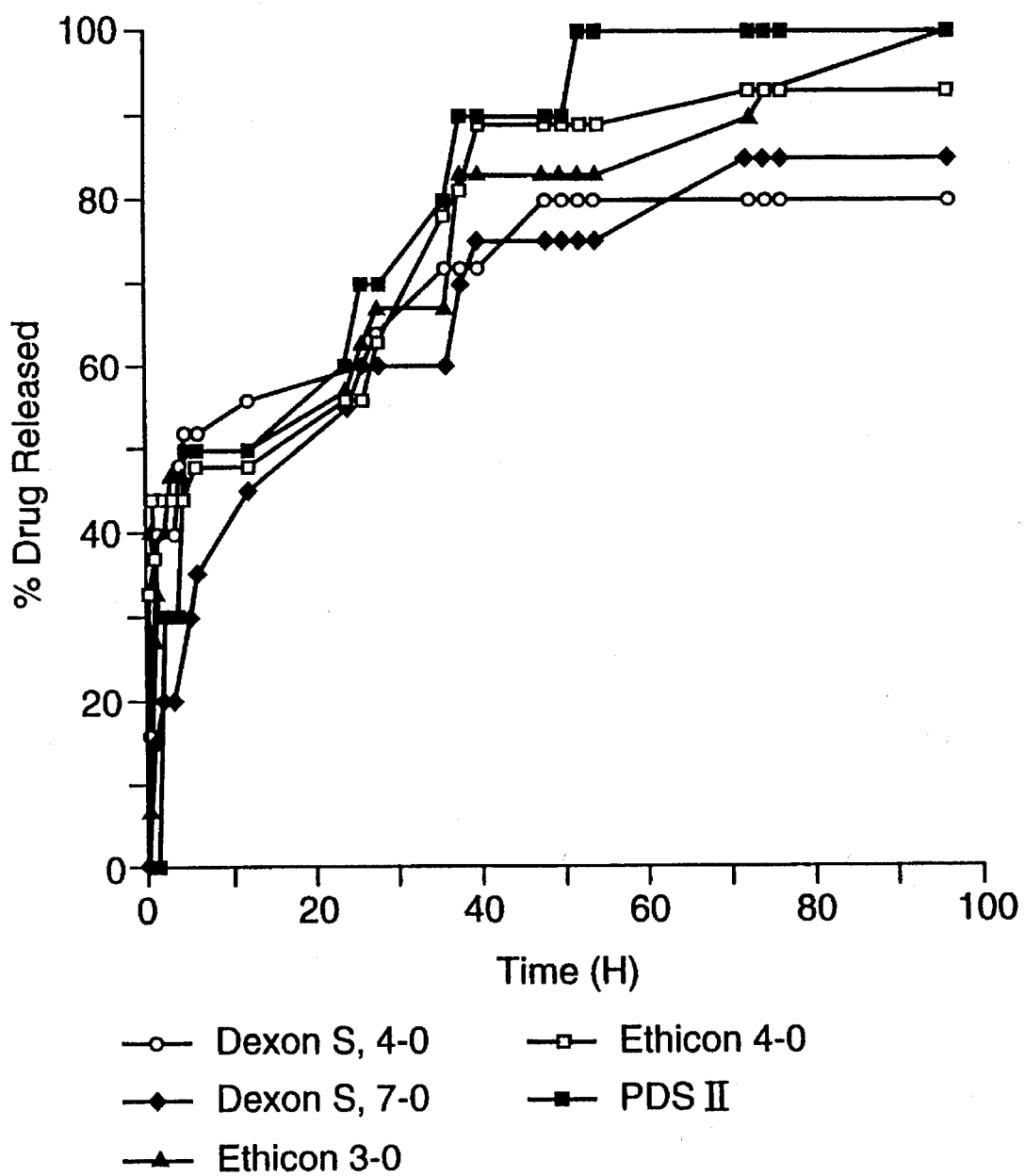
FIG. 10 is a graphical representation of % drug released versus time (hrs.).

Core Loading and Rate of Drug Release of tetracycline from sutures.
Polyglycolic acid sutures ("Dexon 'S' 4–0" and "Dexon 'S' 7–0" from Davis & Geck, Danbury, Conn.); Coated VICRYL™ undyed braided (Polyglactin 910) suture coated with polyglactin 370 and calcium stearate (–Ethicon 3–0" and "Ethicon 4–0" from Ethicon, Inc., a Johnson & Johnson Company, Somerville, N.J.); and polydioxanone ("PDS-II 0" from Ethicon, Inc., a Johnson & Johnson company, Sommerville, N.J.); were impregnated with tetracycline (Sigma Chemical Co.). Approximately 0.3 g of sutures were placed in an open vial with 2½ to 3 ml of tetracycline saturated water (5 g/20 ml deionized water). The vial was placed in a 300 cc pressure vessel (Newport Scientific, Inc., Jessup, Md.) which was charged with $CO_2$ and adjusted to 14.5 Megapascal(Mpa) (2,100 psi) at 35° C. The system was maintained at this condition for 17 hours before venting down to ambient pressure. The sutures were recovered and rinsed in sterile deionized water. The sutures were towel dried and placed in polyethylene bags in a desiccator until evaluated for core loading and drug release.
Procedure for core loading.
The sutures were dissolved in 10 ml of methylene chloride. 20 ml of methanol was added to the solution. The absorbance of the solution was measured at 360 nm on a Bausch and Lomb Spectronic 20 spectrophotometer. The weight percent core loading was calculated from a standard curve prepared from known concentrations of tetracycline in methylene chloride and methanol. The results are shown in Table 12.
Procedure for evaluating drug release.
The tetracycline loaded sutures (10 mg) were added to 30 ml of buffer (Physiosol Irrigation Solution, pH 6.2) in a 250 ml side-arm flask. The flask and its contents were incubated at room temperature on a rotary shaker at 100 rpm. At time intervals of 15 minutes for the first hour, 1 hour intervals for the first 12 hours, and every twelve hours until 96 hours, the absorbance of the solution was measured at 360 nm using a Bausch and Lomb Spectronic 20 spectrophotometer. The results are shown in FIG. 10. Tetracycline was present in the sutures and was slowly released for 50 hours. Sutures cannot be loaded before formation due to degradation of antibiotics during extrusion of the polymer. Solvent loading sutures after formation destroys the tensile strength of the suture. Therefore, impregnation of the suture using supercritical conditions has an advantage.

TABLE 12

| | Core loading of sutures | |
| --- | --- | --- |
| Example | Suture | Core Loading (wt %) |
| 54 | Dexon "S" 4-0 | 5.6 |
| 55 | Dexon "S" 7-0 | 5.5 |
| 56 | Ethicon 3-0 | 7.0 |
| 57 | Ethicon 4-0 | 7.6 |
| 58 | PDS-II | 0.6 |

Core loading ranged from 0.6 to 7.6 % with a release rate of 2 to 4 days. The suture in Example 58 did not dissolve well, which may explain the lower core loading. The curves in FIG. 10 are similar to each other in that they have an initial burst (50% of drug released at the first timepoint) and then a slower rate of release. The tetracycline release rate was slower than the release rate for gentamicin due to the fact that tetracycline was much less soluble in water than gentamicin.

Consequently, for an understanding of the scope of the present invention, reference is made to the following claims.
What is claimed:
1. A method of impregnating a polymeric substrate with an impregnation additive comprising;
    (a) placing a polymeric substrate into a pressure vessel at atmospheric pressure;
    (b) simultaneously contacting the polymeric substrate with a mixture of a carrier liquid and an impregnation additive, wherein the impregnation additive is substantially insoluble in a supercritical fluid and is selected from the group consisting of insulin, trypsin, gentamicin, and tetracycline;
    (c) sealing the pressure vessel:
    (d) exposing the polymeric substrate and the mixture of the carrier liquid and impregnation additive to the supercritical fluid in the pressure vessel for time sufficient to swell the polymeric substrate such that the carrier liquid and impregnation additive at least partially penetrates the swollen polymeric substrate; and
    (e) releasing the pressure in the pressure vessel so that the carrier liquid diffuses out of the swollen polymeric substrate, wherein an amount of the impregnation additive is trapped within the polymeric substrate.
2. A method of impregnating a polymeric substrate according to claim 1, wherein the carrier liquid further includes a surfactant.

* * * * *

UNITED STATES PATENT AND TRADEMARK OFFICE
CERTIFICATE OF CORRECTION

PATENT NO.: 5,508,060

DATED: April 16, 1996

INVENTOR(S): Perman et al.

It is certified that error appears in the above-identified patent and that said Letters Patent is hereby corrected as shown below:

Col. 14, line 19, Insert --*-- between a and the comma
Col. 14, line 19, Insert --*-- between b and the comma
Col. 15, line 34, Delete "Polypropylone" and insert --Polypropylene--
Col. 16, line 32, Delete "24" and insert --2-4--
Col. 21, line 14, Delete "CFFA) and insert --(TFA)--
Col. 22, line 22-23, Delete "con-vening" and insert --converting--
Col. 24, line 53, Insert a space between 800 and ml
Col. 25, line 39, Insert a space between 100 and ml
Col. 26, line 33, Delete "$CO_2$at" and insert --$CO_2$ at--
Col. 27, line 46, Delete "5"
Col. 29, line 33, Insert a space between 2.5 and ml
Col. 29, line 53, Delete "5"
Col. 30, line 40, Delete "38-36" and insert --28-36--
Col. 30, line 59, Delete "38-36" and insert --28-36--
Col. 30, line 67, Delete "38-36" and insert --28-36--
Col. 31, line 51, Delete "38-36" and insert --28-36--
Col. 32, line 49, Delete "38-36" and insert --28-36--
Col. 33, line 14, Delete "38-36" and insert --28-36--
Col. 33, line 21, Insert a space between "$CO_2$" and "and"
Col. 33, line 46, Delete "(-Ethicon" and insert --("Ethicon--
Col. 33, line 54, Insert a space between "$CO_2$" and "and"

Signed and Sealed this

Thirty-first Day of December, 1996

Attest:

BRUCE LEHMAN

*Attesting Officer*     *Commissioner of Patents and Trademarks*